US012778653B2

(12) United States Patent
LaNeve et al.

(10) Patent No.: US 12,778,653 B2
(45) Date of Patent: *Nov. 3, 2026

(54) APPARATUS FOR MANUAL EXTRACTION OF A MEDICAL DEVICE

(71) Applicant: Pain TEQ, LLC, Tampa, FL (US)

(72) Inventors: Sean LaNeve, Tampa, FL (US); Dwayne Polzer, Lutz, FL (US); Christopher Lee, Tampa, FL (US)

(73) Assignee: Pain TEQ, LLC, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/610,065

(22) Filed: Mar. 19, 2024

(65) Prior Publication Data

US 2024/0261011 A1 Aug. 8, 2024

Related U.S. Application Data

(63) Continuation of application No. PCT/US2023/029556, filed on Aug. 4, 2023, which is (Continued)

(51) Int. Cl.

| | |
|---|---|
| ***A61B 17/92*** | (2006.01) |
| ***A61B 17/02*** | (2006.01) |
| *A61B 17/00* | (2006.01) |

(52) U.S. Cl.

CPC ............ *A61B 17/92* (2013.01); *A61B 17/025* (2013.01); *A61B 2017/00367* (2013.01)

(58) Field of Classification Search

CPC ....................... A61B 17/1671; A61B 17/7086; A61F 2/4603

See application file for complete search history.

(56) References Cited

U.S. PATENT DOCUMENTS

| | | | |
|---|---|---|---|
| 4,569,338 | A | 2/1986 | Edwards |
| 5,334,205 | A | 8/1994 | Cain |

(Continued)

FOREIGN PATENT DOCUMENTS

| | | |
|---|---|---|
| AU | 726979 | 10/1998 |
| AU | 756550 | 5/2002 |

(Continued)

OTHER PUBLICATIONS

"Captiva Spine, TransFasten Posterior Sacroiliac (SI) Joint Fusion System", available at: https://web.archive.org/web/20230610175036/https://transfasten.captivaspine.com/si-joint-surgeon-providers/, last visited on Feb. 10, 2026.

(Continued)

*Primary Examiner* — Andrew Yang

(74) *Attorney, Agent, or Firm* — Knobbe, Martens, Olson & Bear, LLP

(57) ABSTRACT

A joint decorticator instrument configured for single use. The joint decorticator has a metal rod affixed within a polymer sheath. The polymer sheath has a longitudinal channel configured to receive an alignment protrusion with a working channel for maintaining the joint decorticator in a proper alignment relative to the working channel. The joint decorticator may include an integrated extraction mechanism involves an extraction lever pivotally connected to the handle portion of the polymer sheath. The extraction lever has an eccentric cam mechanism. When the extraction lever is pivoted toward an open position, the cam exerts a force onto a collar of the working channel and an opposite force on the connector pin that pivotally connects the extraction lever to the polymer sheath, thereby dislodging the abrading head of the joint decorticator from the joint.

18 Claims, 22 Drawing Sheets

Related U.S. Application Data a continuation-in-part of application No. 18/221,347, filed on Jul. 12, 2023, now Pat. No. 11,931,053.

(60) Provisional application No. 63/395,270, filed on Aug. 4, 2022.

(56) References Cited

U.S. PATENT DOCUMENTS 5,676,699 A 10/1997 Gogolewski
5,722,978 A 3/1998 Jenkins, Jr.
6,053,916 A 4/2000 Moore
6,080,155 A 6/2000 Michelson
6,371,988 B1 4/2002 Pafford et al.
6,436,098 B1 8/2002 Michelson
6,648,917 B2 11/2003 Gerbec et al.
6,652,533 B2 11/2003 O'Neil
6,770,074 B2 8/2004 Michelson
6,846,327 B2 1/2005 Khandkar et al.
7,018,416 B2 3/2006 Hanson et al.
7,125,425 B2 10/2006 Foley et al.
7,229,477 B2 6/2007 Biscup
7,390,327 B2 6/2008 Collazo et al.
7,648,509 B2 1/2010 Stark
7,837,732 B2 11/2010 Zucherman et al.
8,016,829 B2 9/2011 Mahoney et al.
8,021,392 B2 9/2011 Petersen
8,025,684 B2 9/2011 Garcia-Bengochea et al.
8,128,700 B2 3/2012 Delurio et al.
8,157,865 B2 4/2012 Hochschuler et al.
8,162,981 B2 4/2012 Vestgaarden
8,197,513 B2 6/2012 Fisher et al.
8,221,503 B2 7/2012 Garcia et al.
8,287,572 B2 10/2012 Bae et al.
8,348,950 B2 1/2013 Assell et al.
8,349,015 B2 1/2013 Bae et al.
8,382,843 B2 2/2013 Laurence et al.
8,403,991 B2 3/2013 Ullrich, Jr. et al.
8,551,171 B2 10/2013 Johnson et al.
8,556,900 B2 10/2013 Yoko et al.
8,579,912 B2 11/2013 Isaza et al.
8,617,244 B2 12/2013 Reichen et al.
8,623,053 B2 1/2014 Vestgaarden
8,623,054 B2 1/2014 McCormack et al.
8,740,912 B2 6/2014 Stark
8,753,345 B2 6/2014 McCormack et al.
8,753,347 B2 6/2014 McCormack et al.
8,821,555 B2 9/2014 Bae et al.
8,828,062 B2 9/2014 McCormack et al.
8,834,472 B2 9/2014 McCormack et al.
8,845,727 B2 9/2014 Gottlieb et al.
8,882,818 B1 11/2014 Vestgaarden
8,906,025 B2 12/2014 Yoko et al.
8,906,028 B2 12/2014 Kleiner et al.
8,945,224 B2 2/2015 Trieu
8,961,571 B2 2/2015 Lee et al.
8,979,928 B2 3/2015 Donner
9,005,288 B2 4/2015 McCormack et al.
9,011,492 B2 4/2015 McCormack et al.
9,017,407 B2 4/2015 Donner
9,101,371 B2 8/2015 Assell et al.
9,113,919 B2 8/2015 Assell et al.
9,119,732 B2 9/2015 Schifano et al.
9,138,275 B2 9/2015 Bae et al.
9,149,283 B2 10/2015 Assell et al.
9,161,763 B2 10/2015 Assell et al.
9,168,152 B2 10/2015 Raiszadeh et al.
9,186,155 B2 11/2015 Katzman et al.
9,220,606 B2 12/2015 Janowski et al.
9,241,798 B2 1/2016 Petersen
9,247,943 B1 2/2016 Kleiner
9,254,198 B2 2/2016 Laurence et al.
9,320,529 B2 4/2016 Yoko et al.
9,333,090 B2 5/2016 Donner et al.
9,345,525 B2 5/2016 Yoko et al.
9,375,243 B1 6/2016 Vestgaarden
9,421,109 B2 8/2016 Donner
9,451,986 B2 9/2016 Stoffman
9,492,284 B2 11/2016 Ginn et al.
9,498,349 B2 11/2016 Patterson et al.
9,526,626 B2 12/2016 Hansell et al.
9,615,856 B2 4/2017 Arnett et al.
9,622,791 B2 4/2017 McCormack et al.
9,629,665 B2 4/2017 McCormack et al.
9,662,128 B2 5/2017 Reiley
9,668,781 B2 6/2017 Stark
9,675,363 B2 6/2017 Abbasi
9,700,356 B2 7/2017 Donner et al.
9,717,602 B2 8/2017 Laurence et al.
9,757,154 B2 9/2017 Donner et al.
9,795,396 B2 10/2017 Donner et al.
9,801,732 B2 10/2017 Chin et al.
9,808,346 B2 11/2017 Stark
9,826,986 B2 11/2017 Donner et al.
9,833,321 B2 12/2017 Rindal
9,838,874 B2 12/2017 Lee et al.
9,895,176 B2 2/2018 Vestgaarden
9,949,843 B2 4/2018 Reiley et al.
10,004,547 B2 6/2018 Reiley et al.
10,070,970 B2 9/2018 Lynn et al.
10,123,849 B2 11/2018 Greenhalgh et al.
10,136,932 B2 11/2018 Freese
10,136,995 B2 11/2018 Donner et al.
10,149,673 B2 12/2018 McCormack et al.
10,149,764 B2 12/2018 Stark
10,166,033 B2 1/2019 Reiley et al.
10,194,962 B2 2/2019 Schneider et al.
10,195,053 B2 2/2019 Kleiner et al.
10,201,427 B2 2/2019 Mauldin
10,206,739 B2 2/2019 Godara et al.
10,219,841 B1 3/2019 Compton et al.
10,219,912 B2 3/2019 Suh et al.
10,226,285 B2 3/2019 McCormack et al.
10,245,044 B2 4/2019 Petersen
10,245,158 B2 4/2019 Song
10,265,176 B2 4/2019 Donner et al.
10,271,959 B2 4/2019 Bae et al.
10,292,720 B2 5/2019 Donner
10,314,710 B2 6/2019 Donner et al.
10,321,945 B2 6/2019 Schifano et al.
10,357,368 B2 7/2019 Aksu
10,363,140 B2 7/2019 Mauldin et al.
10,398,425 B2 9/2019 Mahoney et al.
10,426,539 B2 10/2019 Schifano et al.
10,456,175 B2 10/2019 McCormack et al.
10,492,802 B2 12/2019 Donner et al.
10,507,119 B2 12/2019 Laubert et al.
10,543,105 B2 1/2020 Greenhalgh et al.
10,555,818 B2 2/2020 McConnell et al.
10,568,666 B2 2/2020 McCormack et al.
10,588,672 B2 3/2020 McCormack et al.
10,646,258 B2 5/2020 Donner et al.
10,653,535 B2 5/2020 McCormack et al.
10,660,763 B2 5/2020 Wilson et al.
10,682,150 B2 6/2020 Stark
10,736,752 B1 8/2020 Schifano et al.
10,744,003 B2 8/2020 Ryan et al.
10,751,196 B1 8/2020 Schifano et al.
10,765,532 B2 9/2020 Ashleigh et al.
10,779,958 B2 9/2020 Lines
10,820,917 B2 11/2020 Sharifi-Mehr et al.
D905,232 S 12/2020 Schifano et al.
10,849,764 B2 12/2020 Moore et al.
10,864,021 B2 12/2020 Marik et al.
10,952,749 B2 3/2021 Abbasi
10,993,757 B2 5/2021 Schifano et al.
D922,568 S 6/2021 Schifano et al.
11,020,129 B2 6/2021 LaNeve et al.
11,058,550 B2 7/2021 LaNeve et al.
11,058,556 B2 7/2021 LaNeve et al.
11,083,511 B2 8/2021 Schifano et al.
11,129,718 B2 9/2021 Donner et al.
11,141,144 B2 10/2021 McCormack et al.
11,154,402 B1 10/2021 LaNeve et al.
11,160,667 B2 11/2021 Laurence et al.

(56) References Cited

U.S. PATENT DOCUMENTS 11,172,939 B2 11/2021 Donner et al.
11,272,964 B2 3/2022 McCormack et al.
11,344,339 B2 5/2022 McCormack et al.
11,364,129 B2 6/2022 Hovda et al.
11,376,026 B2 7/2022 Donner et al.
11,376,132 B2 7/2022 LaNeve et al.
11,382,755 B2 7/2022 LaNeve et al.
11,382,770 B2 7/2022 LaNeve et al.
11,389,305 B2 7/2022 LaNeve et al.
D972,137 S 12/2022 Schifano et al.
11,534,406 B2 12/2022 Oliveira Varum et al.
11,547,424 B2 1/2023 Ries
11,559,408 B2 1/2023 McCormack et al.
11,583,416 B2 2/2023 Greenhalgh et al.
11,627,971 B2 4/2023 LaNeve et al.
11,653,935 B2 5/2023 LaNeve et al.
11,666,362 B2 6/2023 Compton et al.
11,717,416 B2 8/2023 LaNeve et al.
11,737,884 B2 8/2023 Vestgaarden et al.
11,931,053 B2 3/2024 LaNeve et al.
11,963,883 B2 4/2024 LaNeve et al.
12,121,458 B2 10/2024 LaNeve et al.
12,161,562 B2 12/2024 LaNeve et al.
12,409,042 B2 9/2025 Vestgaarden et al.
2001/0000532 A1 4/2001 Michelson
2001/0031967 A1 10/2001 Nicholson et al.
2002/0143400 A1 10/2002 Biscup
2004/0133279 A1 7/2004 Krueger et al.
2005/0075640 A1 4/2005 Collazo et al.
2005/0080422 A1 4/2005 Otte et al.
2005/0090829 A1 4/2005 Martz et al.
2005/0165420 A1 7/2005 Cha
2005/0240195 A1 10/2005 Axelson, Jr. et al.
2005/0251146 A1 11/2005 Martz et al.
2006/0054171 A1 3/2006 Dall
2006/0089633 A1 4/2006 Bleich et al.
2006/0178673 A1 8/2006 Curran et al.
2007/0156241 A1 7/2007 Reiley et al.
2007/0233131 A1 10/2007 Song et al.
2007/0276406 A1 11/2007 Mahoney et al.
2008/0009861 A1 1/2008 Stark
2008/0063622 A1 3/2008 Zamora
2008/0082173 A1 4/2008 Delurio et al.
2008/0091270 A1 4/2008 Miller
2008/0154374 A1 6/2008 Labrom
2008/0249569 A1 10/2008 Waugh et al.
2009/0024174 A1 1/2009 Stark
2009/0076551 A1 3/2009 Petersen
2009/0099610 A1 4/2009 Johnson et al.
2009/0177205 A1 7/2009 McCormack et al.
2009/0216238 A1 8/2009 Stark
2009/0259261 A1 10/2009 Reiley
2009/0312763 A1 12/2009 McCormack et al.
2011/0098817 A1 4/2011 Eckhardt
2011/0106261 A1 5/2011 Kingsley et al.
2011/0184518 A1 7/2011 Trieu
2011/0238181 A1 9/2011 Trieu
2011/0264229 A1 10/2011 Donner
2012/0083883 A1 4/2012 Ginn
2012/0259365 A1 10/2012 Richelsoph
2012/0277801 A1 11/2012 Marik
2013/0006364 A1 1/2013 McCormack et al.
2013/0006368 A1 1/2013 Walsh et al.
2013/0018474 A1 1/2013 McCormack et al.
2013/0023995 A1 1/2013 McCormack et al.
2013/0023996 A1 1/2013 McCormack et al.
2013/0030440 A1 1/2013 McCormack et al.
2013/0030532 A1 1/2013 McCormack et al.
2013/0144296 A1 6/2013 Yoko et al.
2013/0144350 A1 6/2013 Yoko et al.
2013/0173004 A1 7/2013 Greenhalgh et al.
2013/0218215 A1 8/2013 Ginn et al.
2013/0325020 A1 12/2013 Yoko et al.
2014/0031935 A1 1/2014 Donner et al.
2014/0081279 A1 3/2014 Kleiner et al.
2014/0088711 A1 3/2014 Kingsley et al.
2014/0207191 A1 7/2014 Kornel
2014/0277204 A1 9/2014 Sandu
2014/0277460 A1 9/2014 Schifano
2014/0288565 A1 9/2014 McCormack
2014/0288602 A1 9/2014 McCormack et al.
2015/0012097 A1 1/2015 Ibarra et al.
2015/0025534 A1 1/2015 Gordan et al.
2015/0073552 A1 3/2015 To et al.
2015/0080976 A1 3/2015 Yoko et al.
2015/0094765 A1 4/2015 Donner et al.
2015/0112444 A1 4/2015 Aksu
2015/0230937 A1 8/2015 Voellmicke
2015/0250611 A1 9/2015 Schifano et al.
2015/0250612 A1 9/2015 Schifano et al.
2015/0328012 A1 11/2015 Hansell et al.
2016/0030191 A1 2/2016 McLuen et al.
2016/0175113 A1 6/2016 Lins
2016/0278818 A1 9/2016 Donner et al.
2016/0310197 A1 10/2016 Black et al.
2017/0245999 A1 8/2017 Ginn et al.
2017/0348027 A1 12/2017 McCormack et al.
2017/0354444 A1 12/2017 McCormack et al.
2017/0367846 A1 12/2017 Greenhalgh et al.
2018/0036017 A1 2/2018 Donner et al.
2018/0085491 A1 3/2018 Erbe
2018/0092748 A1 4/2018 Donner et al.
2018/0161077 A1 6/2018 McCormack et al.
2018/0177608 A1 6/2018 Greenhalgh et al.
2018/0303624 A1 10/2018 Shoshtaev
2019/0021868 A1 1/2019 Ludwig et al.
2019/0083271 A1 3/2019 Donner et al.
2019/0090888 A1 3/2019 Sand et al.
2019/0133613 A1 5/2019 Reiley et al.
2019/0209151 A1 7/2019 McCormack et al.
2019/0254840 A1 8/2019 Gray et al.
2019/0262010 A1 8/2019 Cerundolo et al.
2019/0328429 A1 10/2019 McCormack et al.
2019/0336292 A1 11/2019 Aksu
2019/0343640 A1 11/2019 Donner et al.
2020/0029979 A1 1/2020 Donner et al.
2020/0060733 A1 2/2020 Compton et al.
2020/0085475 A1 3/2020 McCormack et al.
2020/0085480 A1 3/2020 Schifano et al.
2020/0093612 A1 3/2020 Blain et al.
2020/0121375 A1 4/2020 Schifano et al.
2020/0138452 A1 5/2020 Gatrell et al.
2020/0138589 A1 5/2020 Abbasi
2020/0179135 A1 6/2020 Castro
2020/0214724 A1 7/2020 Donner et al.
2020/0253619 A1 8/2020 Gregory
2020/0315811 A1 10/2020 Cryder et al.
2020/0337856 A1 10/2020 Moore et al.
2020/0390566 A1 12/2020 Murray et al.
2021/0015502 A1 1/2021 Sharifi-Mehr et al.
2021/0022881 A1 1/2021 McCormack et al.
2021/0228360 A1 7/2021 Hunt
2021/0236146 A1 8/2021 Donner et al.
2021/0386434 A1 12/2021 Tanaka et al.
2022/0031297 A1 2/2022 McCormack et al.
2022/0151663 A1 5/2022 McCormack et al.
2022/0280303 A1 9/2022 Mauldin et al.
2022/0287742 A1 9/2022 McCormack et al.
2022/0313334 A1 10/2022 Schifano et al.
2023/0076180 A1 3/2023 Schifano et al.
2023/0149179 A1 5/2023 McCormack et al.
2023/0157734 A1 5/2023 McCormack et al.
2023/0363927 A1 11/2023 LaNeve et al.
2025/0009396 A1 1/2025 Vestgaarden
2025/0099260 A1 3/2025 LaNeve et al.
2025/0248746 A1 8/2025 Vestgaarden
2025/0302508 A1 10/2025 Lewis et al.

FOREIGN PATENT DOCUMENTS

CN 110123436 8/2019
EP 1290985 4/2008
EP 1713408 9/2010
EP 2328492 3/2018

(56) References Cited

FOREIGN PATENT DOCUMENTS

| | | |
|---|---|---|
| EP | 2702952 | 4/2018 |
| EP | 3326556 | 5/2018 |
| EP | 2877128 | 6/2018 |
| FR | 2727004 | 5/1996 |
| WO | WO 2002/034168 | 5/2002 |
| WO | WO 2014/091454 | 6/2014 |
| WO | WO 2017/066443 | 4/2017 |
| WO | WO 2018/195406 | 10/2018 |
| WO | WO 2019/137626 | 7/2019 |
| WO | WO 2019/179653 | 9/2019 |
| WO | WO 2021/067951 | 4/2021 |
| WO | WO 2021/067956 | 4/2021 |
| WO | WO 2021/067962 | 4/2021 |
| WO | WO 2021/067965 | 4/2021 |
| WO | WO 2021/188823 | 9/2021 |
| WO | WO 2022/159837 | 7/2022 |
| WO | WO 2024/030654 | 2/2024 |
| WO | WO 2024/254613 | 12/2024 |

OTHER PUBLICATIONS

Cohen, "Sacroiliac joint pain: A comprehensive review of anatomy, diagnosis, and treatment", Review Article, vol. 101:1440-1453, International Anesthesia Research Society U.S. (2005).
Giannikas et al., "Sacroiliac joint fusion for chronic pain: a simple technique avoiding the use of metalwork", Journal, vol. 13:253-256 (2003).
Final Written Decision, dated Sep. 18, 2024 in IPR2023-000625.
Decision Granting Institution of Inter Partes Review, IPR2023-00625, dated Sep. 20, 2023.

APPARATUS FOR MANUAL EXTRACTION OF A MEDICAL DEVICE

CROSS-REFERENCE TO RELATED APPLICATION

This non-provisional patent application is a continuation of and claims priority to a Patent Cooperation Treaty (PCT) Application No. PCT/US23/29556 filed on Aug. 4, 2023, which claims priority to the U.S. Non-Provisional application Ser. No. 18/221,347 filed on Jul. 12, 2023, which claims priority to the U.S. Provisional Application No. 63/395,270 filed on Aug. 4, 2022, the contents of which are incorporated herein by reference in their entireties. This non-provisional patent application is also a continuation-in-part of and claims priority to the U.S. Non-Provisional application Ser. No. 18/221,347 filed on Jul. 12, 2023, which claims priority to the U.S. Provisional Application No. 63/395,270 filed on Aug. 4, 2022.

BACKGROUND

(1) Field of Endeavor

The present invention relates generally to the field of medical devices, and more particularly, to a single-use joint decorticator apparatus and a method of use thereof.

(2) Description of Related Art

Minimally invasive posterior sacroiliac joint fusion procedures are effective at alleviating back pain. These procedures are performed using a set of surgical instruments that includes a working channel, a joint dilator, a joint decorticator, and an implant inserter. As the demand for the posterior sacroiliac joint fusion procedures grows, availability of surgery-ready instruments often becomes a limiting factor with respect to the frequency at which these procedures can be performed. After every procedure, reusable surgical instruments must undergo a sterilization process, which requires an autoclave and associated equipment. The autoclaving process is time consuming and expensive. Thus, there is an unresolved need for mass-produced, single-use surgical instruments that are surgery-ready on-demand.

Another unresolved need associated with sacroiliac joint fusion procedures pertains to extracting a joint decorticator from the joint. During a surgery, it is common for a joint decorticator to become lodged within a patient's joint. A common technique for extracting a lodged surgical instrument requires a surgeon to use a slide hammer connected to the proximal end of the surgical instrument. According to this technique, the surgeon grasps the hammer sleeve and repeatedly impacts the slide stop of the hammer by forcibly sliding the sleeve along the hammer shaft. However, the effectiveness of the slide hammer often depends on the slide having adequate mass to deliver the requisite impact force, and the heavy slide can cause the entire instrument to become unwieldy during use. Thus, the hammer shaft may exhibit wobbling behavior during the extraction procedure. Because the hammer shaft is connected to the surgical instrument, which is positioned within the working channel, the wobbling of the slide hammer may cause the surgical instrument, and even the working channel, to move erratically. Even a small degree of erratic movement may significantly decrease the amount of control the surgeon has over the surgical instrument, may cause an injury to the patient, and may displace the working channel.

Accordingly, what is needed is an improved, surgery-ready joint decorticator having an integrated extraction mechanism that facilitates safe and efficient extraction of the joint decorticator from a patient's joint and removal thereof via the working channel.

SUMMARY OF THE PREFERRED EMBODIMENTS

In the preferred embodiment, the system and instruments described herein comprises a working channel, a joint dilator, a joint decorticator, an extraction tool, and an implant inserter. The joint decorticator has a polymer sheath with a lumen. The polymer sheath has a distal end, a proximal end, and is configured to be inserted within the working channel to provide access to the joint. A metal rod with a first end and a second end is disposed within the lumen of the polymer sheath. An abrading head is disposed on the first end of the metal rod and extends beyond the distal end of the polymer sheath. The abrading head has abrading surfaces that are used to decorticate cortical bone tissue within the joint. The polymer sheath has a longitudinal channel for slidably receiving an alignment protrusion of the working channel, when the decorticator apparatus is inserted therein. The longitudinal channel and the alignment protrusion work together to prevent rotation of the decorticator apparatus relative to the working channel and the joint.

The decorticator apparatus may include an extraction lever that is affixed to the polymer sheath. The extraction lever and the polymer sheath collectively define a handle of the joint decorticator. The extraction lever has a cam mechanism for retracting the decorticator apparatus from the working channel. When the extraction lever is transitioned from a closed position toward an open position, the cam mechanism of the extraction lever applies a retractive force onto the joint decorticator, thereby retracting the abrading head of the joint decorticator into the working channel and extracting the abrading head from the joint.

In an embodiment, an extraction tool is provided to facilitate extraction of the decorticator apparatus from the joint. The extraction tool can be used as a lever to simultaneously apply opposing forces to the decorticating apparatus and the working channel causing them to separate. In an embodiment, the extraction tool is configured to sequentially engage and apply a retractive force onto a first engagement surface of the decorticating apparatus, and then engage and apply a retractive force onto a second engagement surface of the decorticating apparatus, thereby incrementally extracting the decorticating apparatus from the working channel.

In an embodiment, the invention pertains to a method of preparing a joint for receiving a fusion implant. A working channel is positioned within the joint, providing a passage thereto. The abrading head of the decorticator apparatus is inserted into the working channel. The longitudinal channel with the polymer sheath receives an alignment protrusion of the working channel, thereby properly aligning the decorticator apparatus relative to the working channel. The decorticating apparatus is then advanced into the working channel. The abrading head of the decorticator apparatus is then driven into the joint thereby abrading cortical bone tissue within the joint. If necessary, an impact disk of the decorticator apparatus may be stricken with an impactor. The decorticator apparatus is then extracted using the extraction lever and cam mechanism. If necessary, the extraction tool is used to complete the extraction of the decorticator apparatus.

DESCRIPTION OF THE PREFERRED EMBODIMENT

With reference to the drawings, the novel and non-obvious surgical instrument having an integrated extraction mechanism will now be described with regard for the best mode and the preferred embodiment. The following discussion presents the surgical instrument in the context of the sacroiliac joint. However, the embodiments disclosed herein are meant for illustration and not limitation of the invention. An ordinary practitioner will appreciate that it is possible to create many variations of the following embodiments without undue experimentation, and the instruments described herein can be used with surgical procedures at locations other than the sacroiliac joint.

Surgical Instrument Kit

Figure 1:
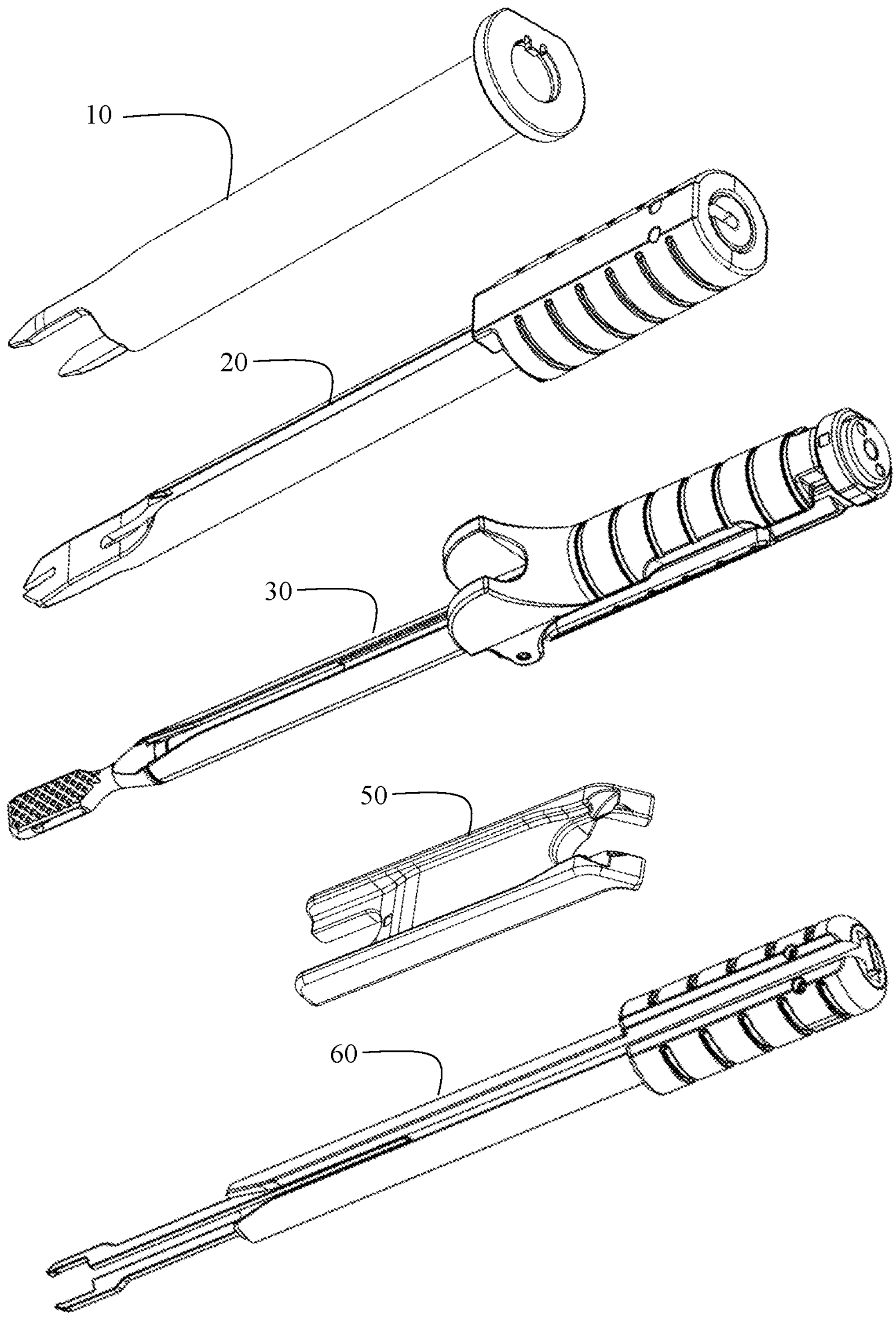
FIG. 1 depicts an embodiment of a surgical instrument set for performing a sacroiliac joint fusion procedure.

FIG. 1 depicts an embodiment of a surgical instrument kit for performing a minimally invasive, posterior sacroiliac joint fusion procedure. The kit includes a working channel 10, a joint dilator 20, a joint decorticator 30, an extraction tool 50, and an implant inserter 60. An ordinary practitioner will appreciate that each of these instruments has a length and a longitudinal axis that extends along the length. As used herein, the term “angular” and similar terms means rotation or rotational displacement about a longitudinal axis. In some aspects these surgical tools are similar to the surgical tools disclosed in U.S. Pat. Nos. 11,020,129; 11,058,556; and 11,058,550, all of which are incorporated herein by reference, in their entireties.

Working Channel

Figure 2A:
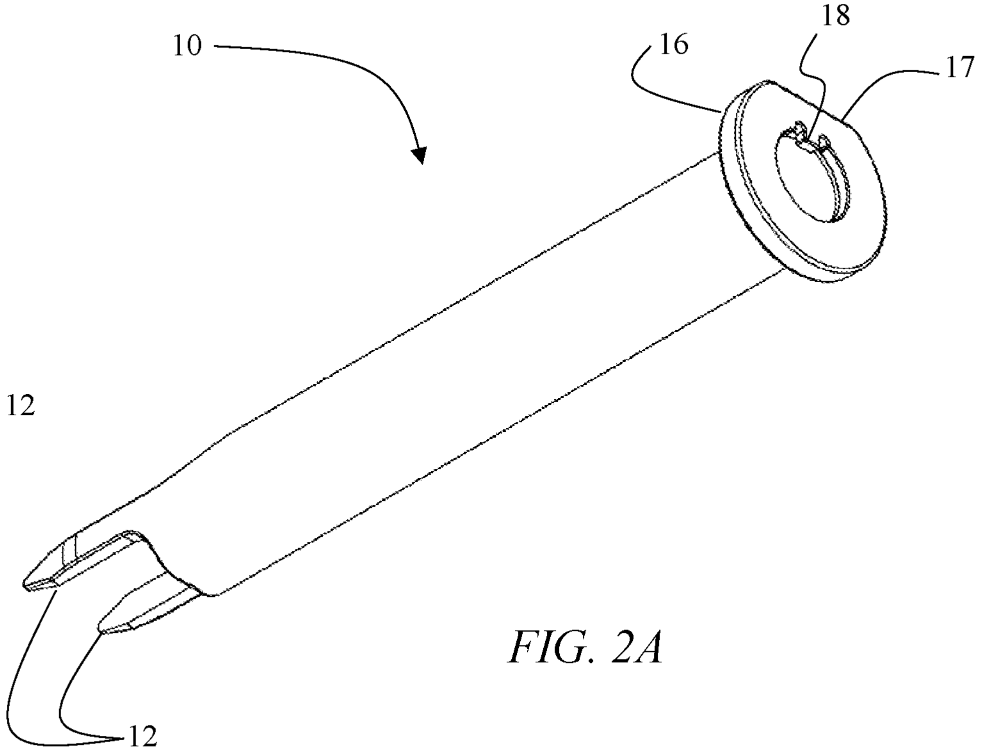
FIG. 2A is a perspective view of an embodiment of a working channel.
Figure 2B:
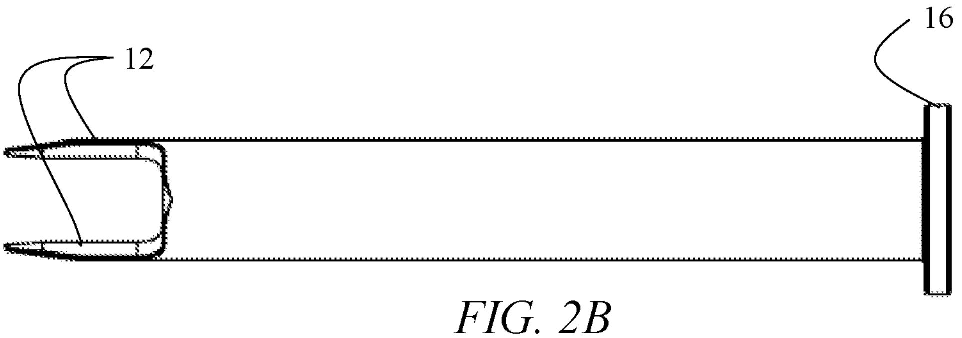
FIG. 2B is a top view of the embodiment of the working channel.
Figure 2C:
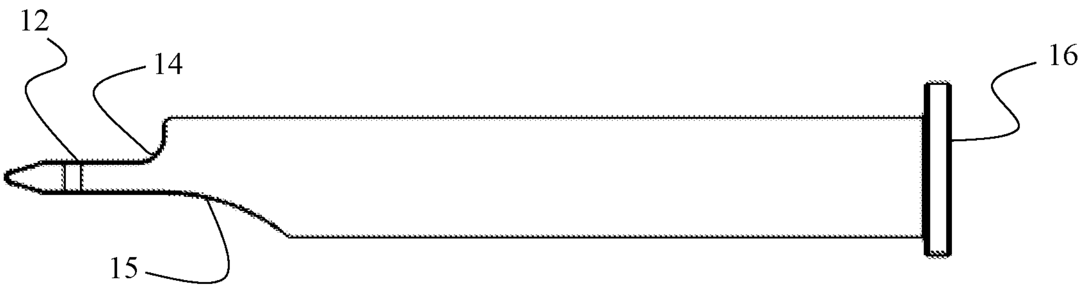
FIG. 2C is a side view of the embodiment of the working channel.

FIGS. 2A-2C depict a working channel 10 according to an embodiment of the invention. The working channel 10 has a pair of arms 12 configured for insertion between a patient’s sacrum and ilium. The arms 12 interface with the working channel 10 in a manner that defines a sacral contour 14 and an iliac contour 15, which are configured for abutment against the sacrum and ilium, respectively. The working channel 10 has a collar 16. The collar 16 has a flat edge 17 aligned with the iliac contour 15, providing a visual and tactile reference indicating the angular orientation of the working channel 10. An alignment protrusion 18 is disposed within the collar 16 and serves as a keyway feature to maintain surgical instruments inserted into the working channel 10 in a predetermined angular orientation relative thereto.

The exemplary dual-material construction of the surgical instruments described herein substantially reduced the cost of the instruments, making them suitable for single-use. In this manner, upon completion of a surgery the surgical instruments are discarded rather than sterilized in an autoclave. This single-use feature provides a major advantage over the state of the art by enabling medical facilities that do not have autoclaves to perform sacroiliac joint fusion procedures. In addition, by adequately stocking the single-use surgical instrument sets, a medical facility can readily ensure on-demand availability of surgery-ready instruments.

The term “metal” as used herein represents an exemplary first materials, and this term broadly encompasses metal and metal alloys suitable for human surgeries—for example, stainless steel or titanium. The term “polymer” as used herein broadly encompasses various polymers suitable for human surgeries, including plastics and fiber-reinforced polymers. Polymers are discussed herein as an exemplary second material, which could also be graphite, carbon fiber, or other suitable materials that are distinct from the first material.

Joint Dilator

Figure 3A:
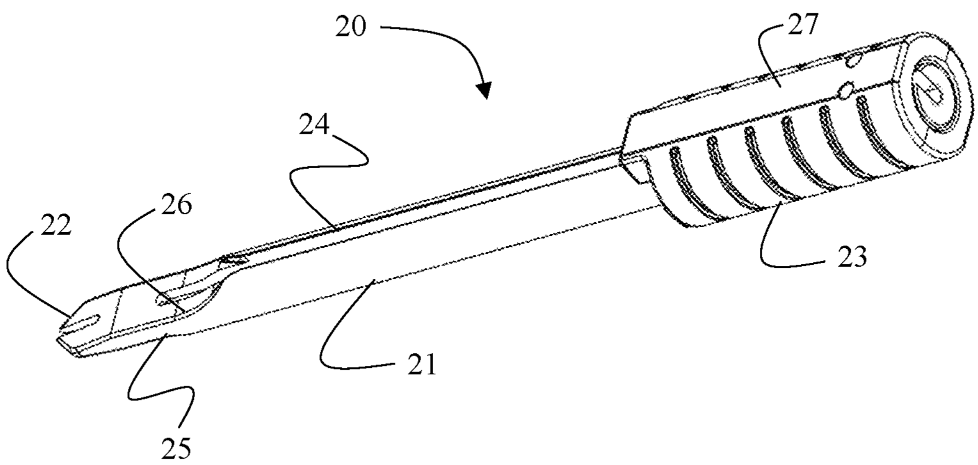
FIG. 3A is a perspective view of an embodiment of a joint dilator.
Figure 3B:
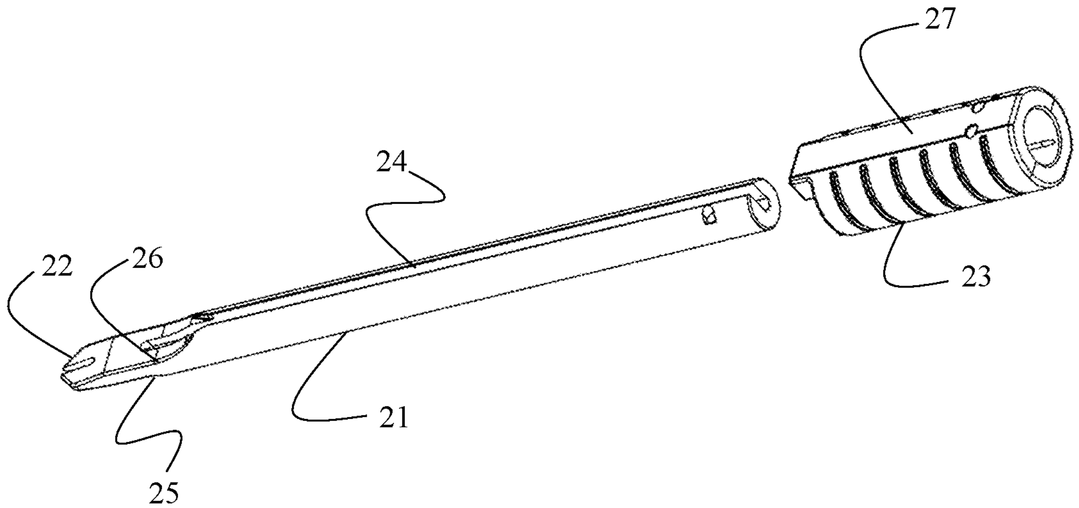
FIG. 3B is a perspective exploded view of the embodiment of the joint dilator.
Figure 3C:
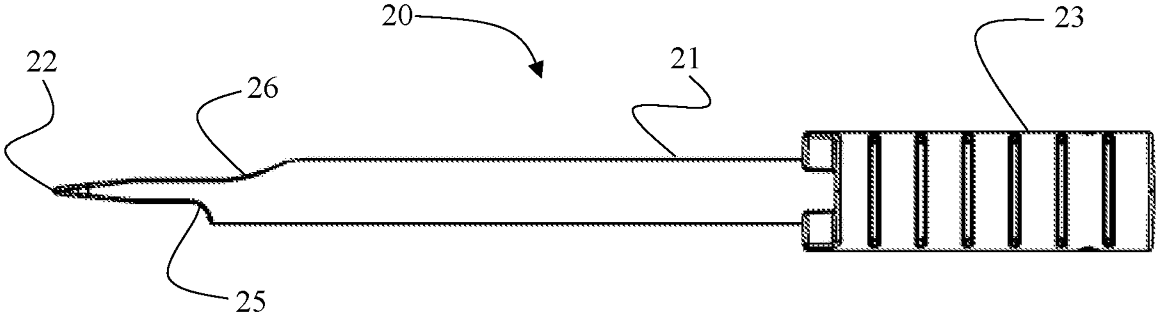
FIG. 3C is a side view of the embodiment of the joint dilator.

FIGS. 3A-3C depict an embodiment of a joint dilator 20. The joint dilator 20 has a generally cylindrical metal body 21. The metal body 21 has a beveled distal end 22 configured for spreading the soft tissue and sliding into a gap between the sacrum and ilium. The leading edge of the beveled distal end 22 is blunt to minimize the possibility of inadvertent penetration into bone tissue during insertion of the joint dilator 20 into the sacroiliac joint. A polymer handle 23 has an inner lumen for receiving the proximal end of the metal body 21 therein. The handle 23 may be affixed to the metal body 21 using fasteners, or any other affixing means known in the art. In an embodiment, the handle 23 has flat surfaces 27 that prevent the joint dilator 20 from rolling when placed on a surgical tray or another support surface. In addition, the flat surfaces 27 provide visual and tactile references with respect to the angular orientation of the joint dilator 20. Furthermore, the flat surfaces 27 enable the joint dilator 20 to be used as an impactor for driving the joint decorticator 30 into the joint, wherein the metal body 21 is functions as a handle, while handle 23 becomes the impactor head.

The metal body 21 has a channel 24 extending its full length or a portion thereof, especially the distal portion thereof. The channel 24 is configured to receive a K-wire therein for guiding the joint dilator 20 toward a predetermined location within the sacroiliac joint. At the distal end 22 of the joint dilator 20, a section of the channel 24 may be fully enclosed to restrict non-axial movement of the K-wire within the channel 24. The remainder of the channel 24 is open to enable the soft tissue and bodily fluids displaced during the insertion of the joint dilator 20 to exit the channel 24. The channel 24 also permits mating alignment with the alignment protrusion 18, as described below.

Figure 4A:
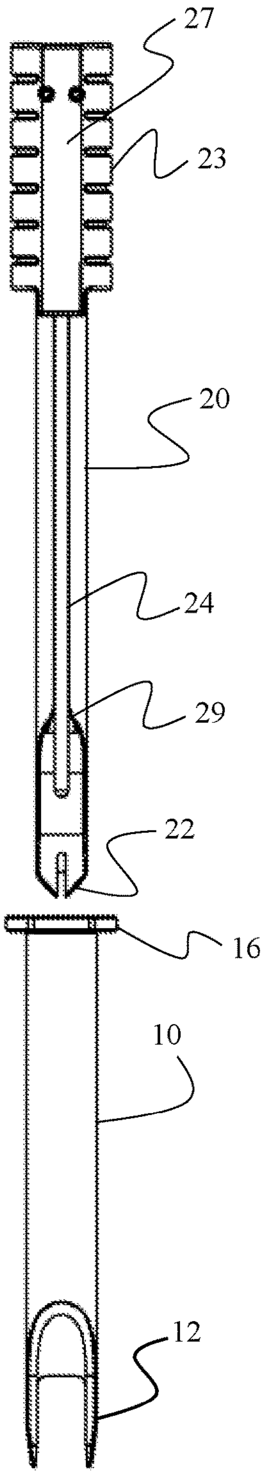
FIG. 4A is the first figure in a sequence depicting a method of inserting a joint dilator into a working channel.
Figure 4B:
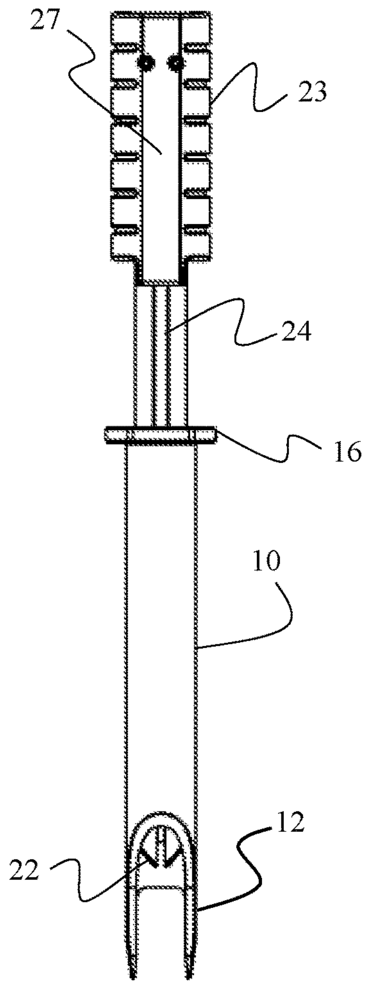
FIG. 4B is the second figure in the sequence depicting the method of inserting the joint dilator into the working channel.
Figure 4C:
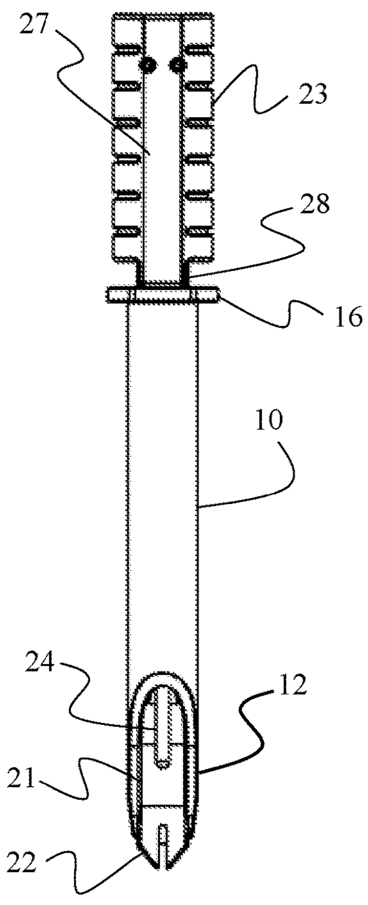
FIG. 4C is the third figure in a sequence depicting the method of inserting the joint dilator into the working channel.
Figure 4D:
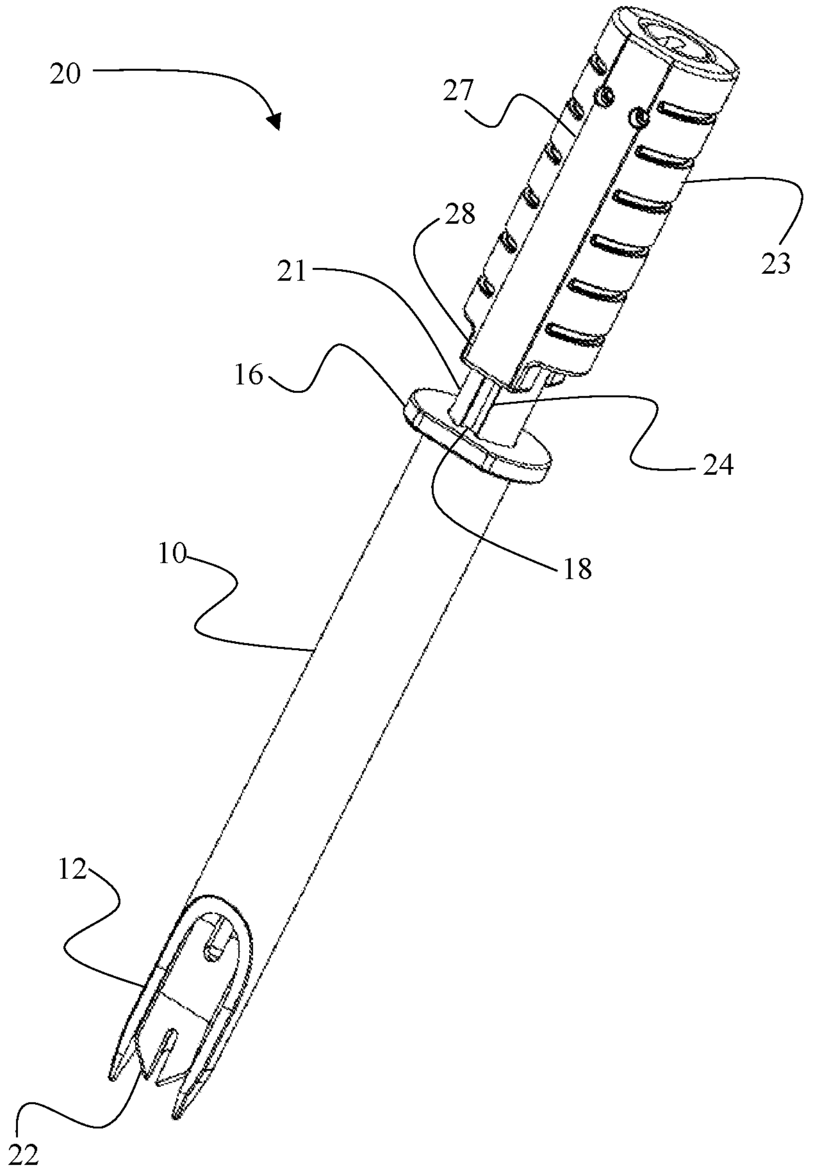
FIG. 4D is perspective view depicting the joint dilator being inserted into the working channel.

FIGS. 4A-4C illustrate the steps of the joint dilator 20 being coupled with the working channel 10 to collectively form a joint dilator assembly. The channel 24 receives the alignment protrusion 18 of the working channel 10 thereby restraining the joint dilator 20 against relative rotation with respect to the working channel 10.

The channel 24 may have a flared section 29—which may be delta-shaped—for helping guide the alignment protrusion 18 into the channel 24. The contours of the flared section 29 are configured to bring the joint dilator 20 into a proper angular alignment with the working channel 10. If the distal end of the joint dilator 20 is advanced into the working channel 10 in an angular position in which the channel 24 is misaligned relative to the guide protrusion 18, engagement between the guide protrusion 18 and the contour of the flared section 29 causes the joint dilator 20 to rotate axially until the guide protrusion 18 becomes aligned with the channel 24 and enters thereinto. In this manner, the flared section 29 functions as an early-alignment mechanism that ensures that the joint dilator 20 is properly aligned with the working channel 10, without requiring that a surgeon must manually align these surgical instruments. Therefore, this early alignment feature eliminates human error and facilitates quick and efficient insertion of the joint dilator 20 into the working channel 10.

The distal end of the joint dilator 20 has sacral and iliac contours 25 and 26 that complement the sacral and iliac contours 12 and 14 of the working channel 10. FIG. 4C depicts that the clearances between the inner surfaces of arms 12 and the metal body 21 are minimal to prevent pinching of soft tissue therebetween. In an embodiment, the lateral walls of the distal end 22 of the joint dilator 20 have convex radii that complement the concave radii of the inner surfaces of arms 12. The joint dilator 20 is fully inserted into the working channel 10 when the handle 23 comes into an abutting contact with the collar 16. In this configuration, the joint dilator 20 and the working channel 10 collectively form the joint dilator assembly for insertion into the sacroiliac joint of the patient via a posterior incision. The joint dilator 20 provides structural support for the arms 12 of the working channel 10 and guides them into their position between the sacrum and ilium.

Upon proper insertion of the arms 12 of the working channel 10 into the sacroiliac joint, the joint dilator 20 is axially extracted from the lumen of the working channel 10. FIG. 4C depicts that the handle 23 is structured such that a notch 28 is formed between the collar 16 and the handle 23. The notch 28 is configured to receive the extraction tool 50, which can be used as a lever to apply an extraction force onto the handle 23, as described in more detail below.

Joint Decorticator

Figure 5A:
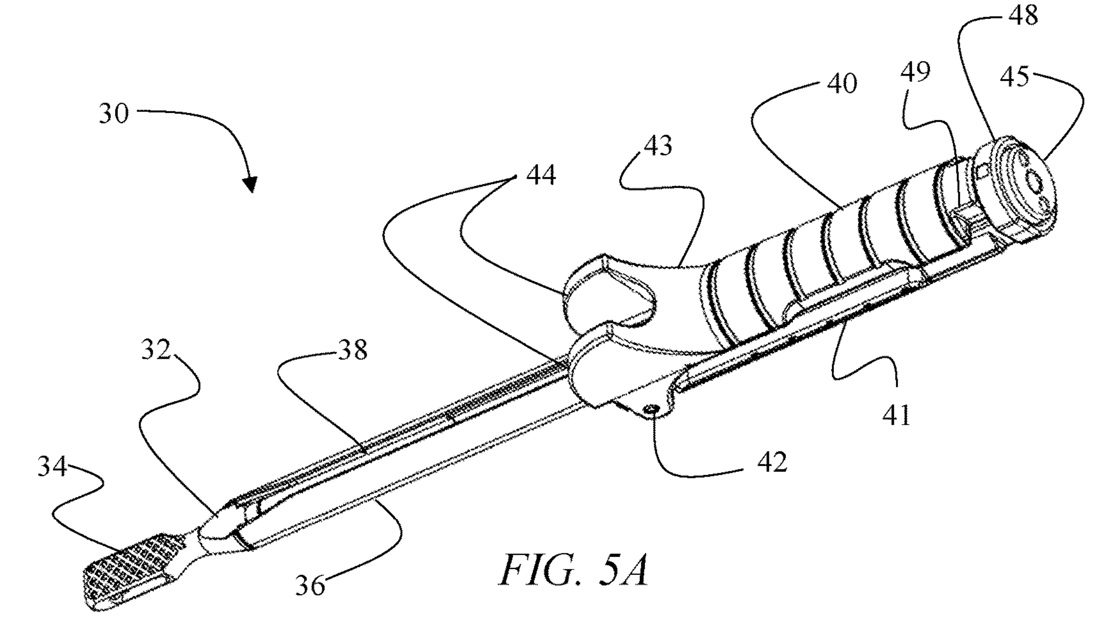
FIG. 5A is a perspective view of an embodiment of a joint decorticator.
Figure 5B:
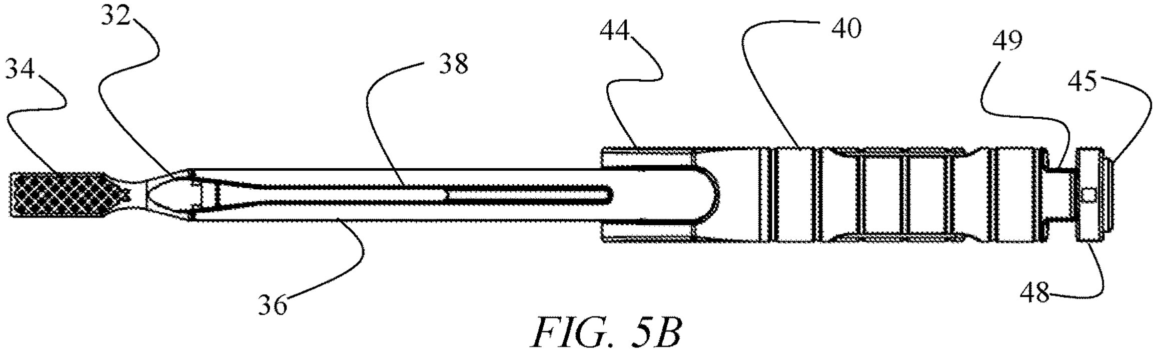
FIG. 5B is a top view of an embodiment of the joint decorticator.
Figure 5C:
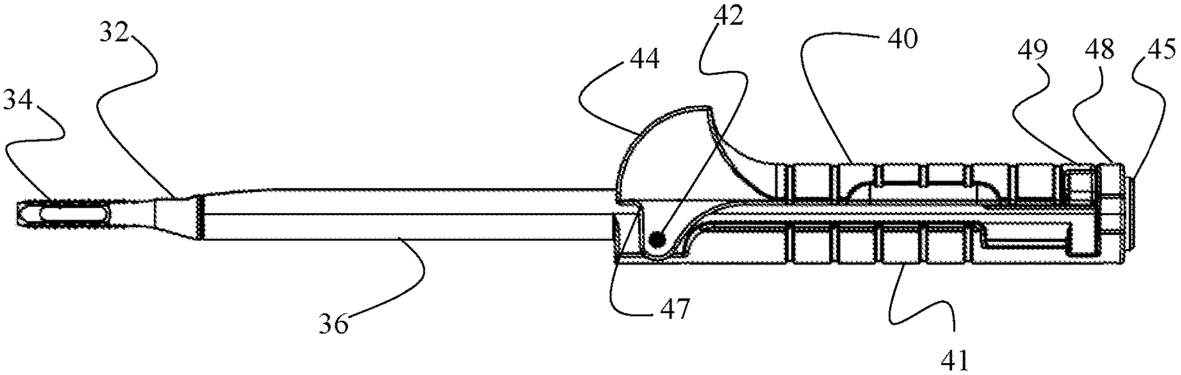
FIG. 5C is a side view of an embodiment of the joint decorticator.
Figure 5D:
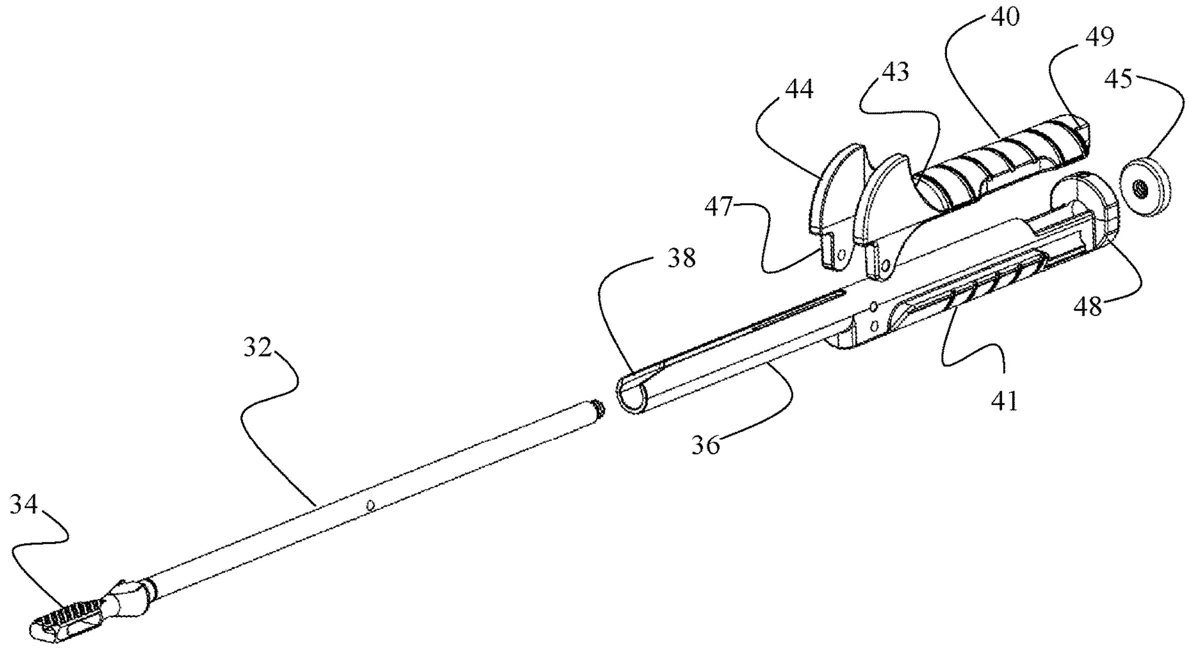
FIG. 5D is a perspective exploded view of an embodiment of the joint decorticator.

FIGS. 5A-5B depict the joint decorticator 30. In an embodiment, the joint decorticator 30 comprises a metal rod 32. The cross-sectional shape of the rod 32 may be circular, rectilinear, or any other shape. An abrading head 34 is disposed at the distal end of the metal rod 32. The abrading head 34 has an open tip with a sharp cutting edge configured to cut bone tissue to create an implant-receiving void within a sacroiliac joint. The cutting edge comprises one or more straight portions and one or more curved portions. The abrading head 34 further comprises abrading surfaces configured to rasp the sacrum and ilium.

The joint decorticator 30 comprises a polymer sheath 36. The polymer sheath 36 has a lumen configured to receive the metal rod 32. The polymer sheath 36 may be affixed to the metal rod 32 using one or more fasteners, or any other fastening means known in the art. The affixed connection between the metal rod 32 and the polymer sheath 36 resists angular displacement between these two components.

In an embodiment, the polymer sheath 36 has a longitudinal channel 38 configured for receiving the alignment protrusion 18 of the working channel 10. The longitudinal channel 38 may be flared at the distal end to help guide the alignment protrusion 18 into the longitudinal channel 38. The flared end may have a delta shape, a rounded shape, or any other shape that results in the distal opening of the longitudinal channel 38 being wider than the remainder of the longitudinal channel 38. This wider portion may be in the shape of a delta, which provides a self-aligning function, similar to that of the corresponding portion of the joint locator 20 described above.

Decorticator Extraction Mechanism

FIGS. 5A-5D depict an extraction lever 40 pivotally connected to the polymer sheath 36 via connector pin 42, which serves as a pivot axis for the extraction lever 40. The extraction lever 40 and a handle portion 41 of the polymer sheath 36 collectively define a handle of the joint decorticator 30, which is configured to be grasped by a surgeon to articulate the joint decorticator 30 during the surgical procedure. The extraction lever 40 has a cam mechanism 44 that is disposed at its distal end. In an embodiment, the cam mechanism 44 comprises two cam-shaped members separated by a distance sufficient to accommodate the width of the polymer sheath 36 during the operation of the cam mechanism 44, as described in more detail below.

Figures 6A, 6B, 6C:
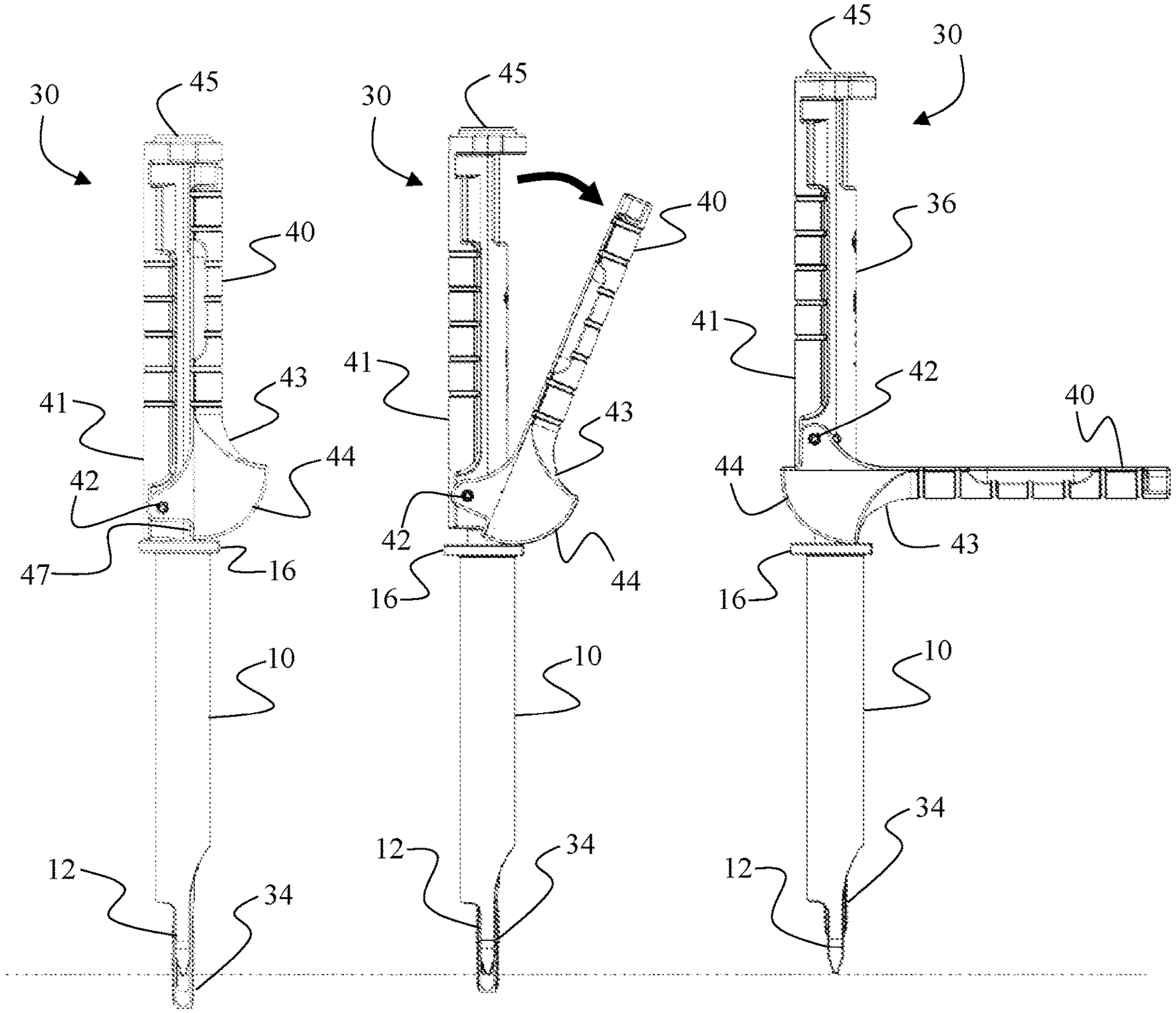
FIG. 6A is the first figure in a sequence depicting a method of extracting the joint decorticator from the working channel using an extraction lever.
FIG. 6B is the second figure in the sequence depicting a method of extracting the joint decorticator from the working channel using the extraction lever.
FIG. 6C is the third figure in the sequence depicting a method of extracting the joint decorticator from the working channel using the extraction lever.

Exemplary operation of an embodiment of the decorticator 30 is shown in FIGS. 6A-6C. FIG. 6A depicts the joint decorticator 30 fully inserted inside a working channel 10. During a surgery, the working channel 10 is inserted into a patient's body such that the distal end of the working channel 10 is positioned at the target surgical site, with the sacral contour 14 and the iliac contour 15 seated against the patient's sacrum and ilium, respectively. The collar 16 at the proximal end of the working channel 10 remains outside the patient's body.

FIG. 6A further depicts that when the joint decorticator 30 if fully inserted into the working channel 10, the extraction lever 40 is in its closed position. In this fully inserted position of the decorticator 30, the abrading head 34 extends out of the lumen of the working channel 10 and is configured to make abrading contact with the sacrum and/or ilium bones of the SI joint, and preferably the respective articular surfaces of these bones. A surgeon drives the abrading head 34 into SI joint by applying an axial force onto the handle of the decorticator 30. In some instances, a surgeon may use an impact tool, such as a mallet or the joint dilator 20, to impact the proximal end of the decorticator 30, thereby driving the abrading head 34 into the SI joint. In an embodiment, an impact disk 45 is affixed to the distal end of the metal rod 32, for example via a screw-threaded engagement. The impact disk 45 protrudes beyond the proximal end of the polymer sheath 36 and provides a striking surface for being impacted with the impactor. The force of the impact is transferred from the impact disk 45 to the abrading head 34 via the metal rod 32.

Due to the forceful insertion of the abrading head 34 into the SI joint, the abrading head 34 may become lodged therein. Extraction of the abrading head 34 must be performed in a controlled manner. Because counter pressure cannot be applied onto the patient's body, extraction of the abrading head 34 by applying a linear force onto the handle 41 of the joint decorticator 30 is impractical.

FIGS. 6A-6C illustrate that the extraction lever 40 can be used to achieve controlled extraction of the abrading head 34 from the SI joint. To dislodge the abrading head 34 from the SI joint, a surgeon may utilize the extraction lever 40 in the following manner: while holding the handle portion 41 of the polymer sheath 36 with one hand, the surgeon would pivot the extraction lever 40 with the other hand toward an open position, as illustrated with an arrow in FIG. 6B. When extraction lever 40 is pivoted about connector pin 42, the cam mechanism 44 exerts opposite forces onto the collar 16 of working channel 10 and the connector pin 42. As the cam mechanism 44 continues transitioning toward its open position depicted in FIG. 6C, the cam mechanism 44 pushes the connector pin 42 further away from the collar 16, thereby causing the abrading head 34 to retract into the working channel 10. After abrading head 34 is dislodged from the SI joint, the abrading tool 10 can be safely removed from the working channel 10 by pulling onto the handle 41.

FIG. 6A depicts that, when the decorticator 30 is fully inserted into the working channel 10, and the abrading head 34 is at its maximum penetration distance relative to the joint—this is the position at which the abrading head 34 is most likely to become lodged within the joint. The cam mechanism 44 is structured such that it provides the greatest mechanical advantage at the beginning of the rotation of the extraction lever 40, thereby resulting in the greater retraction force exerted onto the abrading head 34 to initiate initial dislodgement of the abrading head 34 from the joint.

In an embodiment, to reduce a likelihood of a mechanical failure the extraction lever 40 comprises fillets 43 at the interface of the cam-shaped members of the cam mechanism 44 and the handle portion 40. A person of ordinary skill in the art will recognize that by reinforcing these points of concentrated stress, the likelihood of the cam-shaped members experiencing a structural failure—i.e., fracture of the handle portion of the extraction lever 40—can be decreased. Furthermore, the redundancy achieved by including two cam-shaped members enables the extraction lever 40 to perform its intended function even if one of the cam-shaped members were to experience a structural failure.

Extraction Tool

Figure 7A:
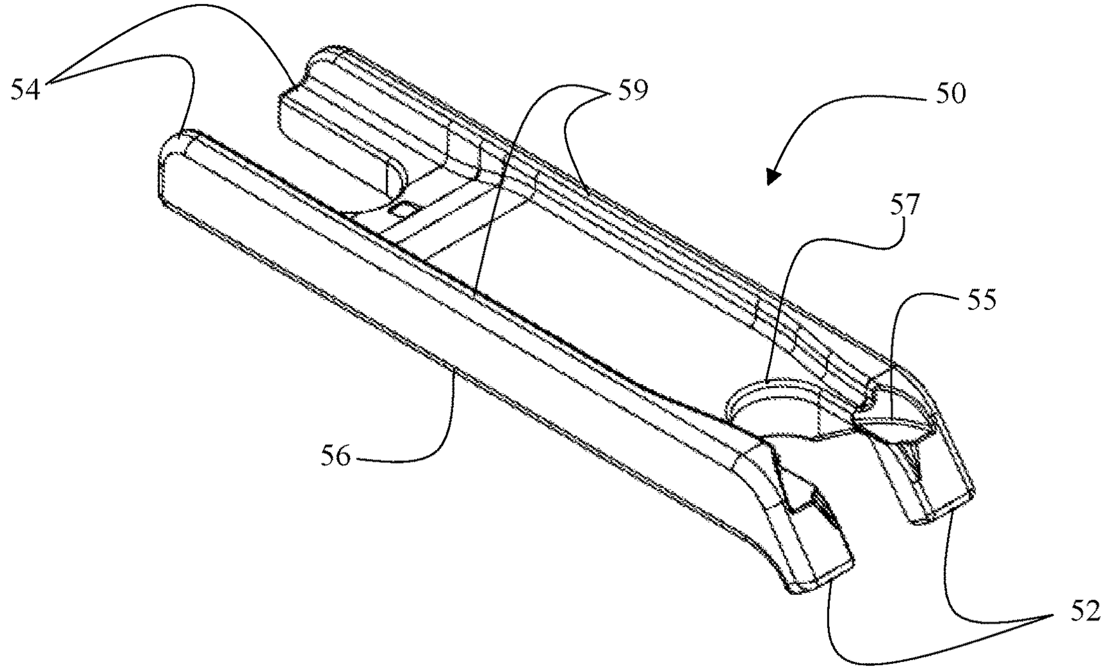
FIG. 7A is a perspective top view of an embodiment of an extraction tool.
Figure 7B:
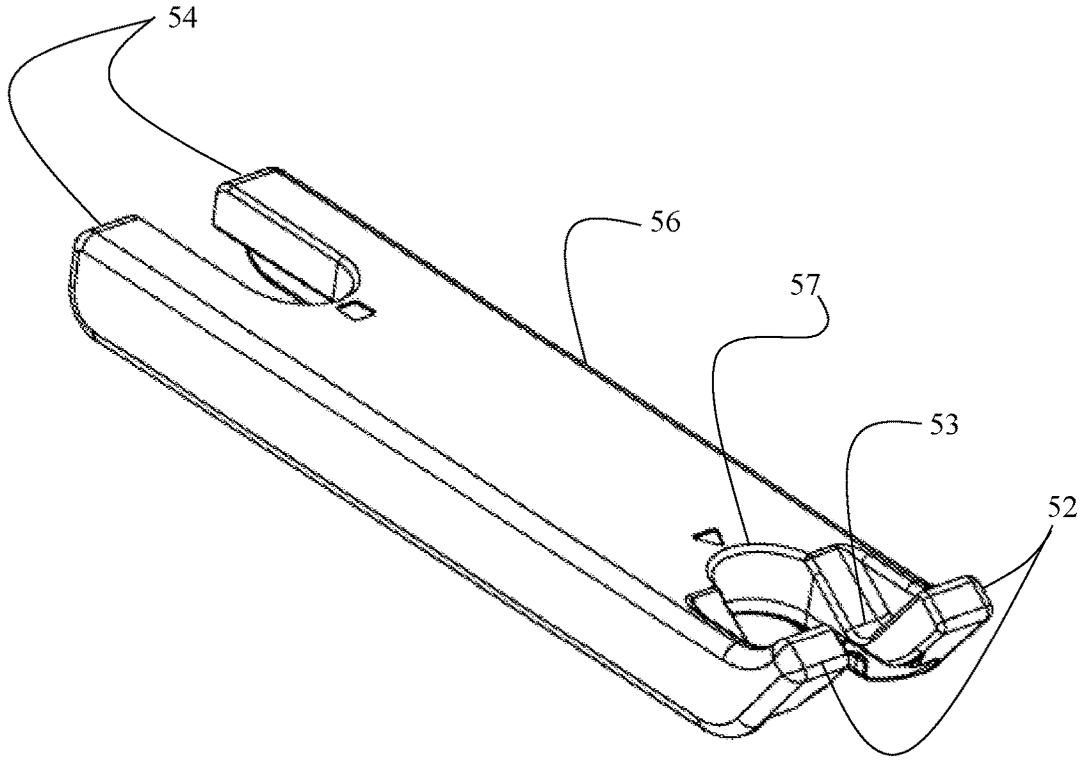
FIG. 7B is a perspective bottom view of an embodiment of an extraction tool.

FIGS. 7A and 7B depict an extraction tool 50 that can be used to dislodge the abrading head 34 of the decorticator 30 from the SI joint. The extraction tool 50 has a first pair of arms 52, a second pair of arms 54, and a body 56. The first pair of arms 52 is disposed at an angle relative to the body 56, while the second pair of arms 54 is straight relative to the body 56.

Figure 8A:
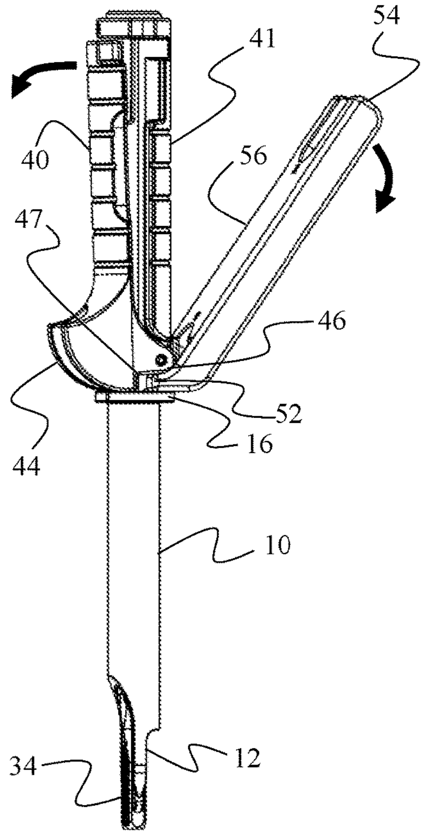
FIG. 8A is the first figure in a sequence depicting a method of using an embodiment of an extraction tool to facilitate extraction of the joint decorticator from a working channel.

FIGS. 8A-8E depict an exemplary extraction procedure using the extraction tool 50. FIG. 8A depicts that the extraction lever 40 has notches 47 shaped to receive the terminal ends of arms 52. To initiate the extraction procedure, a surgeon would insert the arms 52 into the notches 47, such that the angled arms 52 are positioned between the collar 16 of the working channel 10 and the cam mechanism 44. FIG. 7B depicts that the angled arms 52 contain recesses 53, which are shaped to receive the angular contours 46 of the cam mechanism 44, thereby facilitating proper positioning of the angled arms 52 relative to the notches 47.

FIG. 8A depicts that when the angled arms 52 are fully inserted into notches 47, the body 56 and the straight arms 54 of the extraction tool 50 are disposed at an angle relative to the extraction lever 40. FIG. 8A further depicts, that as downward-directed force is applied onto the free end of the extraction tool 50, the collar 16 of the working channel 10 serves as a fulcrum, while the terminal ends of arms 52 of the extraction tool 50 apply an upward force onto the cam mechanism 44 at the notches 47.

Figure 8B:
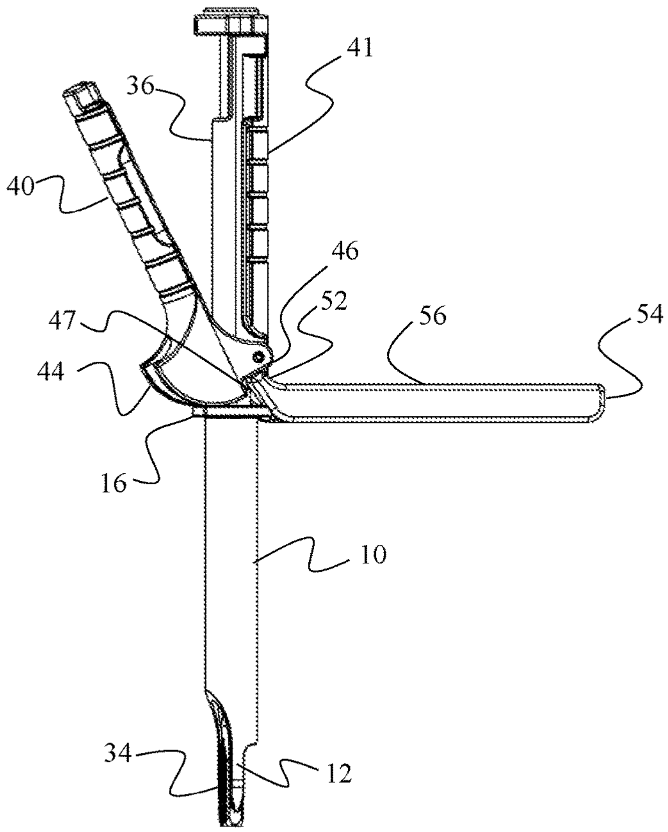
FIG. 8B is the second figure in the sequence depicting a method of using the extraction tool to facilitate extraction of the joint decorticator from the working channel.

As depicted in FIG. 7A, the arms 52 contain rounded notches 55. The contours of the rounded notches 55 match the circumference of the collar 16 of the working channel 10. When the extraction tool 50 becomes orthogonal relative to the working channel 10, as depicted in FIG. 8B, the rounded notches 55 receive the collar 16 therein. This mating engagement between the rounded notches 55 and the collar 16 provides a tactile response to the surgeon that the extraction tool 50 has reached its orthogonal position, signaling to the surgeon to cease application of the downward force onto the extraction tool 50. At this point, the abrading head 34 has likely been sufficiently dislodged from the sacroiliac joint, permitting normal operation of the extraction lever 40 as described above or removal of the joint decorticator 40 via application of a manual linear retraction force onto the handle 41 and the extraction lever 40.

FIGS. 8A and 8B further depict that while applying a downward-directed force onto the extraction tool 50, the surgeon may simultaneously pivot the extraction lever 40 toward its open position. In this manner, the extraction tool 50 functions as an additional lever increasing the magnitude of the oppositely directed forces exerted onto the collar 16 and the connector pin 42, thereby increasing the amount of retractive force applied onto the abrading head 34 of the joint decorticator 30. As the abrading head 34 becomes partially dislodged out the sacroiliac joint via operation of the extraction tool 50, the extraction lever 40 can be operated to fully remove the abrading head 34 from the sacroiliac joint.

Figure 8C:
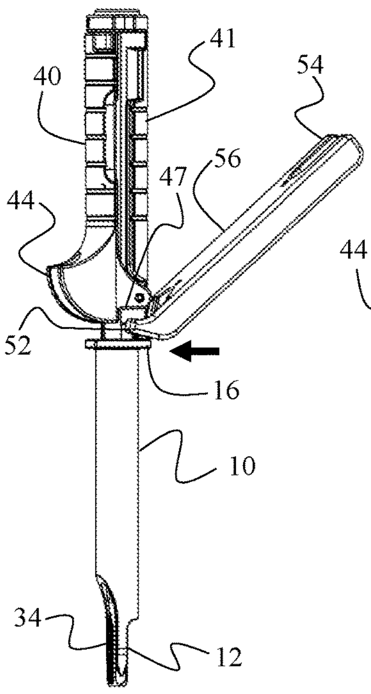
FIG. 8C is the third figure in the sequence depicting a method of using the extraction tool to facilitate extraction of the joint decorticator from the working channel.
Figure 8D:
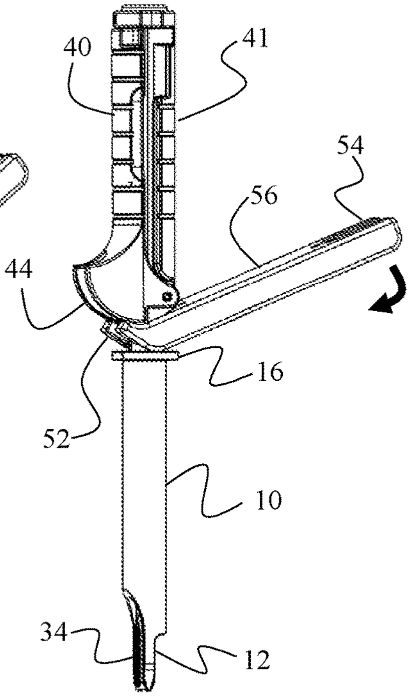
FIG. 8D is the fourth figure the sequence depicting a method of using the extraction tool to facilitate extraction of the joint decorticator from the working channel.
Figure 8E:
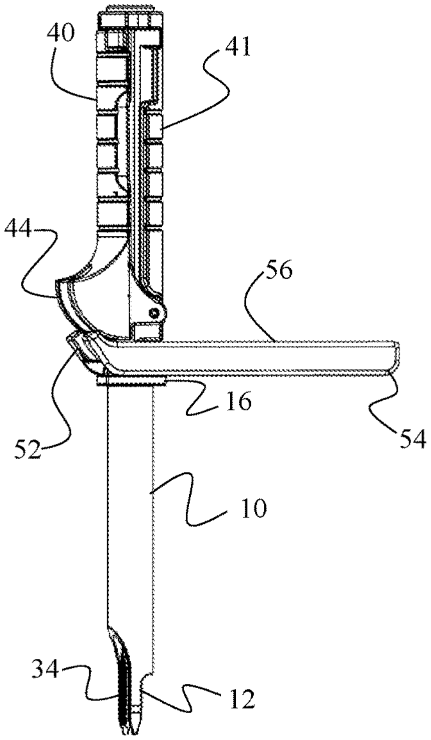
FIG. 8E is the fifth figure in the sequence depicting a method of using the extraction tool to facilitate extraction of the joint decorticator from the working channel.

FIGS. 8C-8E depict the method of using the extraction tool 50 to fully remove the abrading head 34 from the sacroiliac joint without operating the extraction lever 40. This method may be especially useful if the extraction lever 40 were to suffer a fracture or otherwise become inoperative. FIG. 8C depicts that when there is sufficient clearance between the cam mechanism 44 and the collar 16 of the working channel 10, the extraction lever 40 can be closed, and the arms 52 of the extraction tool 50 can be inserted between the collar 16 and the cam mechanism 44. In this configuration, the curved edges of the cam mechanism 44 serve as engagement surfaces for the arms 52. FIG. 8D depicts that after the arms 52 have been positioned between the collar 16 and the cam mechanism 44, the collar 16 of the working channel 10 serves at the fulcrum as the extraction tool 50 is pivoted downward.

FIG. 8E depicts that as the distance between the cam mechanism 44 and the collar 16 increases, the extraction tool 50 can be inserted further therebetween and continue to be used as a lever to continue extraction of the joint decorticator 30 from the working channel 10. The distance between the inner edges of the arms 52 is substantially the same as the diameter of the sheath 36 of the joint decorticator 30, thereby enabling the extraction tool 50 to receive the sheath 36 between the arms 52. In addition, the interface between the arms 52 and the body 56 has a rounded profile 57 with a substantially the same radius as the radius of the sheath 36, thereby providing a snap-type tactile feedback when the rounded profile 57 between the arms 52 engages the sheath 36 when the extraction tool 50 reaches an orthogonal orientation relative to the joint decorticator 30, as depicted in FIG. 8E. In this manner, a surgeon can confidently perform the extraction procedure and rely on this tactile feedback to verify that the instruments are properly oriented with respect to one another and are being used in the intended manner. Thus, the extraction tool 50 functions to enable a two-stage extraction method for removing the abrading head 34 from the sacroiliac joint.

Figures 9A, 9B, 9C, 9D:
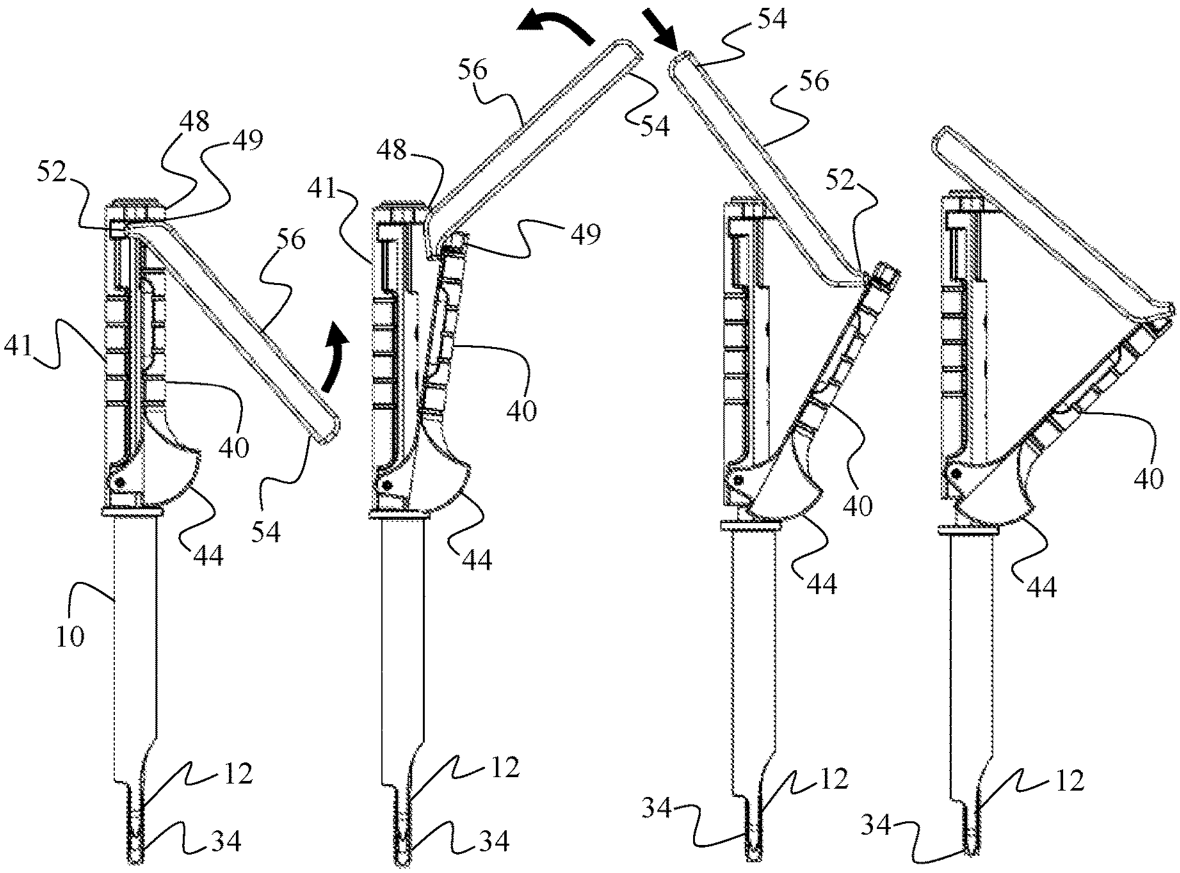
FIG. 9A is the first figure in a sequence depicting a method of using the extraction tool to pry open the extraction lever of the joint decorticator.
FIG. 9B is the second figure in the sequence depicting a method of using the extraction tool to pry open the extraction lever of the joint decorticator.
FIG. 9C is the third figure in the sequence depicting the method of using the extraction tool to pry open the extraction lever of the joint decorticator.
FIG. 9D is the fourth figure the sequence depicting the method of using the extraction tool to pry open the extraction lever of the joint decorticator.

FIGS. 9A-9D depict another method for using the extraction tool 50 to facilitate dislodgement of the abrading head 34 and extraction of the joint decorticator 30. The extraction lever 40 includes notches 49 (most clearly depicted in FIG. 5A-5D) near the proximal end thereof. The extraction tool 50 can be used pry open the extraction lever 40 by engaging the notches 49 and applying an upward force onto the free end of the extraction tool 50. FIG. 9A depicts that the underside of the proximal endplate 48 of the handle 41 functions as a fulcrum, enabling the arms 52 apply a force onto the proximal end of the extraction lever 40. FIGS. 9A and 9B depict that as the angled arms 52 of the extraction tool 50 pivot about the proximal endplate 48, the extraction lever 40 opens, and the cam mechanism 44 retracts the joint decorticator 30 out of the working channel 10 in the manner disclosed above.

FIGS. 9C and 9D depict that to open the extraction lever 40 further, the body of the extraction tool 50 may be positioned such that the proximal endplate 48 of the handle 41 is received between the ridges 59 (depicted in FIG. 7A) extending along both sides of the body 56. The ridges 59 retain the extraction tool 50 in an engagement with the proximal endplate 48 as a linear downward force is applied onto the free end of the extraction tool 50, thereby causing the arms 52 to apply a force onto the extraction lever 40. If needed, an impactor can be used to apply a linear force onto the free end of the extraction tool 50 to fully open the lever 40.

Figure 10:
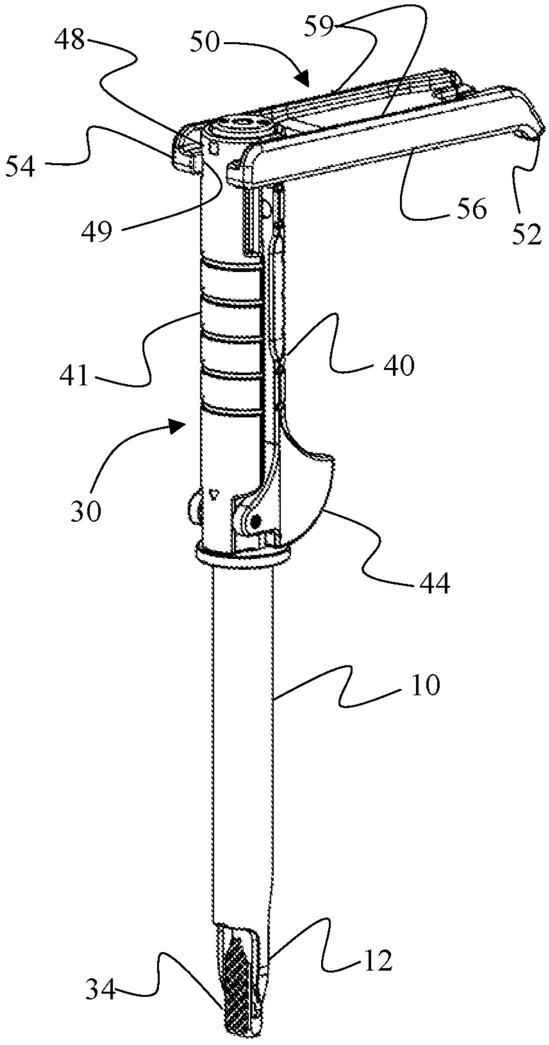
FIG. 10 depicts an additional manner of using an embodiment of the extraction tool to facilitate extraction of the joint decorticator from the working channel.

FIG. 10 depicts yet another way in which the extraction tool 50 can be used to extract the joint decorticator from the working channel 10. The notches 49 of the extraction lever 40 and handle 41 are configured to receive the straight arms 54 of the extraction tool 50 such that the extraction tool 50 extends orthogonally from the longitudinal axis of the joint decorticator 30. In this configuration, the underside surface of the extraction tool 50 can be impacted with a mallet or another impactor (for example, the joint dilator 20) while a surgeon holds the working channel 10 stationary. The arms 54 transfer the applied impact force to the proximal endplate 48 of the handle 41, thereby dislodging the abrading head 34 from the sacroiliac joint and extracting the joint decorticator 30 from the working channel 10, without a need to utilize the cam mechanism 44 of the extraction lever 40.

Implant Inserter

Figure 11A:
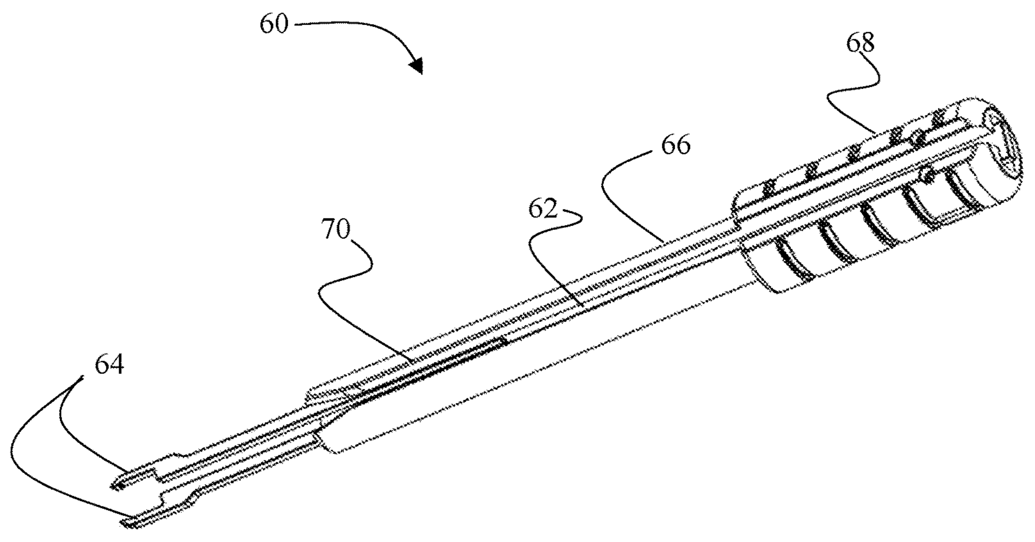
FIG. 11A is a perspective view of an embodiment of an implant inserter.
Figure 11B:
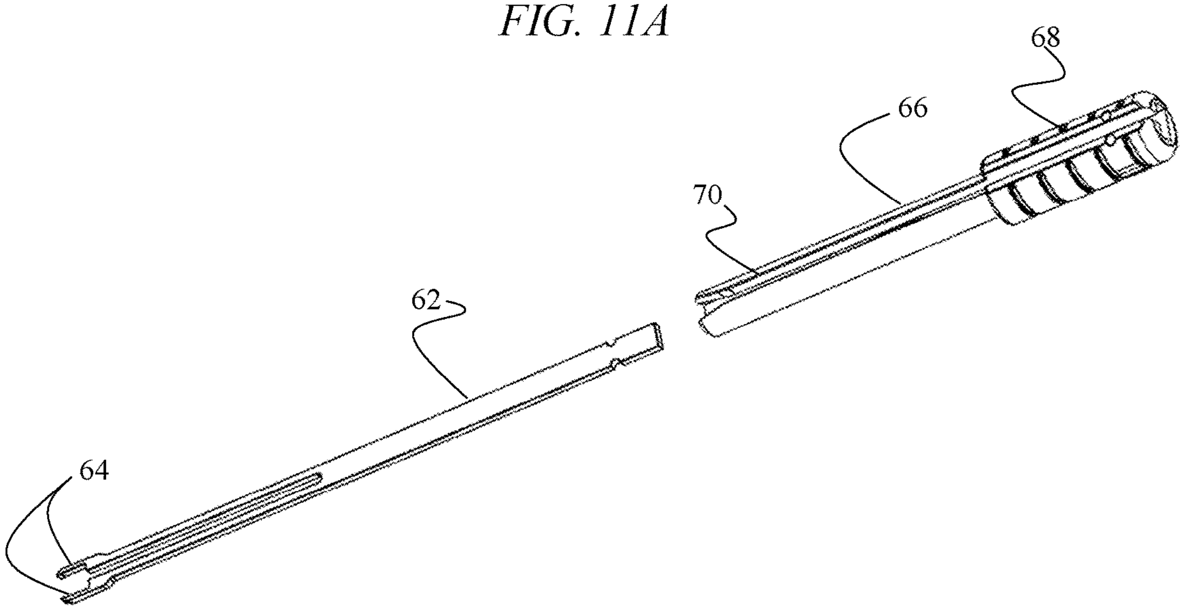
FIG. 11B is a perspective exploded view of an embodiment of the implant inserter.

FIGS. 11A and 11B depict the implant inserter 60. The implant inserter 60 comprises a metal core 62 that terminates with two implant-retaining arms 64. The implant inserter 60 further comprises a polymer sleeve 66. The polymer sleeve 66 has a lumen configured to receive the metal core 62 therein. The polymer sleeve 66 can be affixed to the metal core 62 using fasteners or any other means known in the art. The polymer sleeve has a handle 68 for articulating the implant inserter 50. The implant inserter 50 further has a channel 70 configured to receive the alignment protrusion 18 of the working channel 10 therein, thereby ensuring a predetermined angular alignment between the inserter 60 and the working channel 10. The channel 70 may be flared at the distal end to help guide the alignment protrusion 18 into the channel 38. The flared end may have a delta shape, a rounded shape, or any other shape that results in the distal opening of the channel 70 being wider than the remainder of the channel 70. This wider portion may be in the shape of a delta, which provides a self-aligning function similar to that of the corresponding portion of the joint locator 20 described above.

The resting distance between the arms 64 is less than the width of a fusion implant. Thus, to secure an implant within the arms 64, the arms 64 must undergo an elastic deformation to increase the separation distance therebetween to accommodate the width of the fusion implant. In this manner, when the implant is positioned between the arms 64, they apply a pressure onto the implant, thereby securely retaining the implant therebetween. The juncture at which the implant-retaining arms 64 interface with the metal core 62 is disposed within the polymer sleeve 66, whereby the polymer sleeve 66 restricts the maximum distance by which the arms 64 can be separated, thereby preventing their overextension and potential structural failure.

Additional Joint Decorticator Embodiments

Extraction Tool as the Extraction Lever Extender

Figures 12A, 12B, 12C:
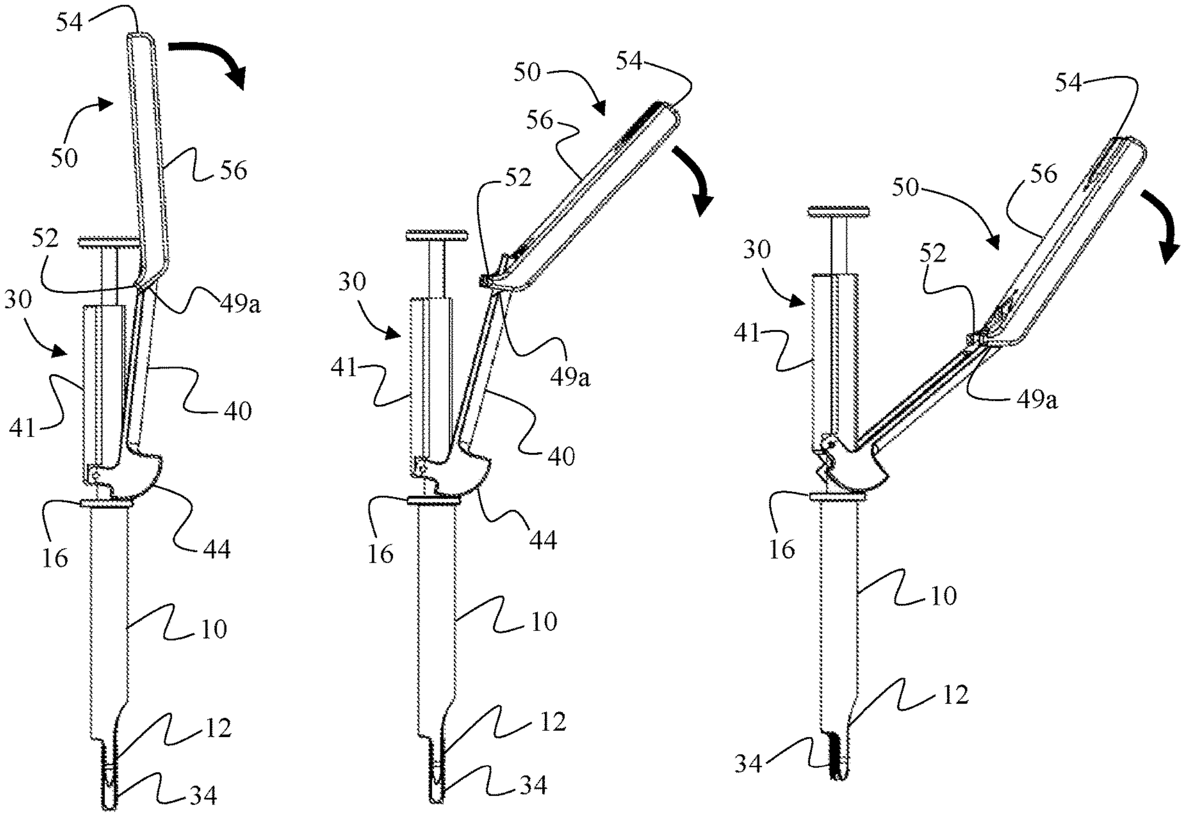
FIG. 12A is the first figure in a sequence depicting a method of using the extraction tool to extend the length of the extraction lever of the joint decorticator.
FIG. 12B is the second figure in the sequence depicting the method of using the extraction tool to extend the length of the extraction lever of the joint decorticator.
FIG. 12C is the third figure in the sequence depicting the method of using the extraction tool to extend the length of the extraction lever of the joint decorticator.

FIGS. 12A-12C depict another method of utilizing the extraction tool 50 to facilitate dislodgement of the abrading head 34 from the sacroiliac joint. The extraction lever 40 of the joint decorticator 30 may include angled notches 49*a* near the proximal end thereof. The notches 49*a* may be configured to receive the arms 52 of the extraction tool 50. In this manner, the effective length of the extraction lever 40 can be extended, thereby reducing the amount of force that the surgeon must apply to transition the extraction lever 40 into its open position.

Dual-Lever Extraction Mechanism

Figure 13A:
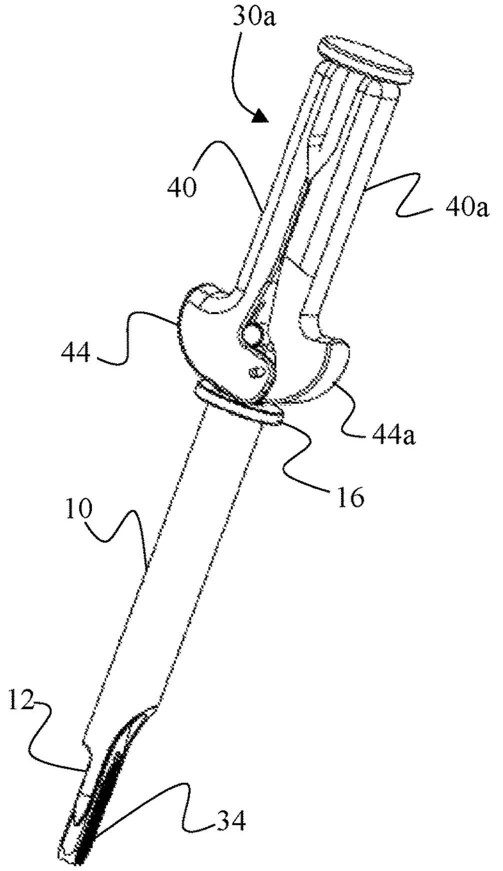
FIG. 13A is a perspective view of an embodiment of the joint decorticator having a dual-lever extraction mechanism, depicting the shaft of the surgical instrument fully inserted into the working channel, with the levers in closed positions and the abrading head protruding from the lumen of the working channel.
Figure 13B:
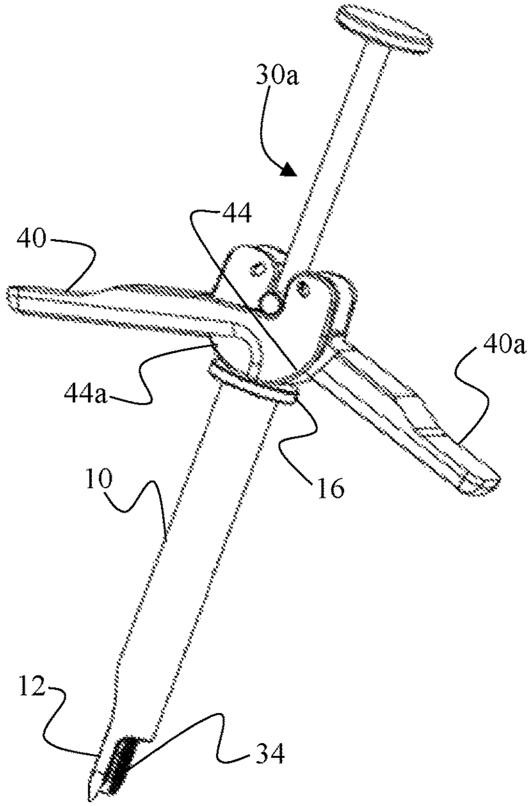
FIG. 13B is a perspective view of the joint decorticator having the dual-lever extraction mechanism, depicting the shaft of the surgical instrument fully inserted into the working channel, with the levers in open positions and the abrading head retracted into the lumen of the working channel.

FIGS. 13A and 13B depict an embodiment of the joint decorticator 30*a* that includes a second extraction lever 40*a* pivotally connected to the handle 41 (the sheath 36 and the handle 41 are not shown in FIGS. 13A and 13B). The second extraction lever 40*a* has a second cam mechanism 44*a*, which may have the same cam radius as the first cam mechanism 44 of the first extraction lever 40. The principle of operation of this dual-lever embodiment is analogous to the principle of operation of the single-lever embodiment described with reference to FIGS. 6A-6C. However, inclusion of the second extraction lever 40*a* provides several advantages. For example, the non-axial components of the forces exerted by the cam mechanism 44 are cancelled out due to the opposite non-axial components exerted by the cam mechanism 44*a* of the second extraction lever 40*a*. In this manner, the net force exerted onto the joint decorticator 30*a* is in an alignment with its longitudinal center axis, thereby increasing the level of precision and control a surgeon has over the joint decorticator 30 during extraction of the abrading head 34 from a sacroiliac joint. Also, inclusion of the second extraction lever 40*a* reduces the stress exerted onto the extraction lever 40, thereby reducing a possibility of a structural failure.

In another embodiment, the two cam mechanisms 44 and 44*a* described above are not symmetrical, meaning that the cam mechanism 44 has a first radius and the second cam mechanism 44*a* has a second radius, wherein at least a portion of the second radius is greater than any portion of the first radius. Thus, the cam mechanism 44 and second cam mechanism 44*a* can be actuated sequentially to deliver a two-stage retraction of the abrading head 34.

Threaded Handle Extraction Mechanism

Figure 14A:
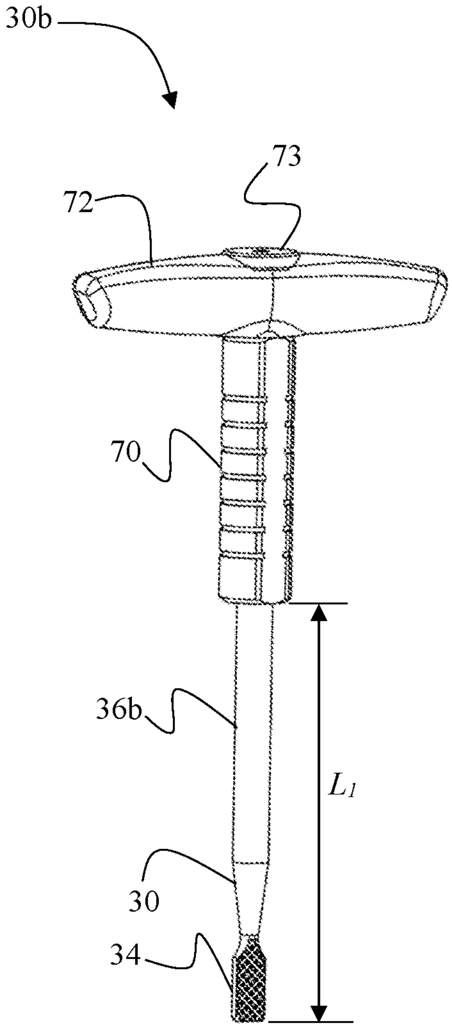
FIG. 14A is a perspective side view an embodiment of the joint decorticator having a threaded-handle extraction mechanism, depicting the threaded handle in the closed position.
Figure 14B:
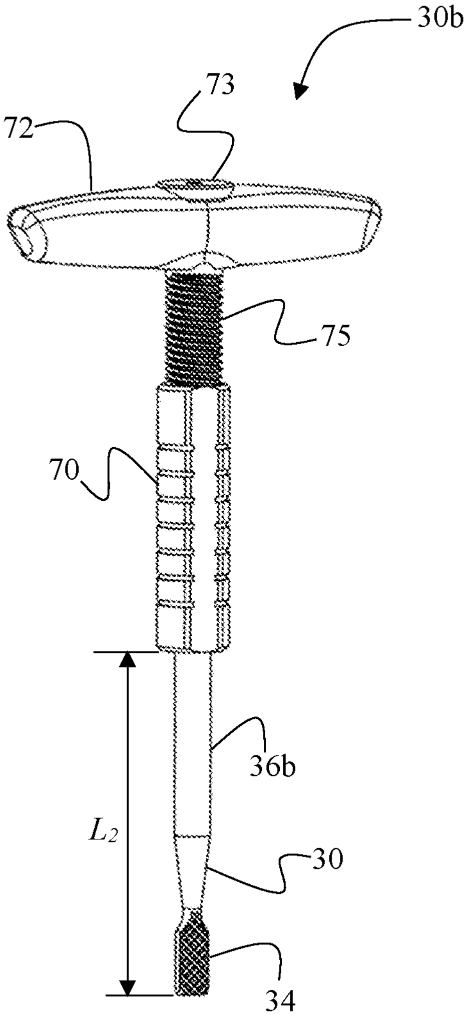
FIG. 14B is a perspective side view of the joint decorticator having the threaded-handle extraction mechanism, depicting the threaded handle in the extended position.
Figure 14C:
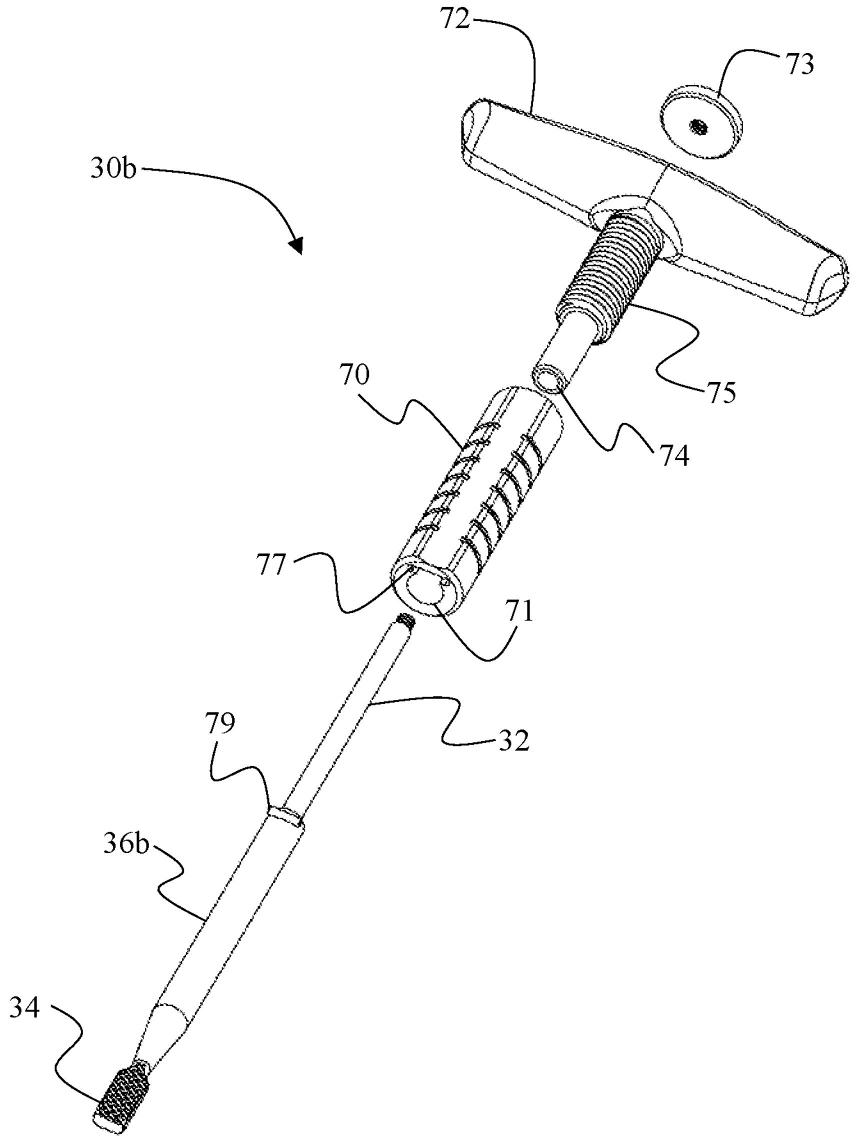
FIG. 14C is a perspective exploded view of the joint decorticator having the threaded-handle extraction mechanism.

FIGS. 14A-14C depict an embodiment of the joint decorticator 30*b* with a threaded extraction handle 72. In this embodiment, the joint decorticator 30*b* comprises a metal rod 32 with an abrading head 34. The metal rod 32 is disposed within a polymer sheath 36*b*. The joint decorticator 30*b* further comprises a handle sleeve 70 having a lumen 71. The sheath 36*b* is slidingly disposed within the handle sleeve 70 and is configured to longitudinally translate therein.

Referring to FIG. 14C, in an embodiment, the distal portion of the lumen 71 may have one or more interior slots 77 configured to receive one or more pins 79 extending from the sheath 36*b*. In this manner, sheath 36*b* and the rod 32 coupled thereto can translate linearly relative to the handle sleeve 70, while being restricted against relative rotation with respect to one another. Alternatively, sheath 36*b* may have one or more longitudinal slots on the exterior surface thereof while the lumen of the handle sleeve 70 may comprise one or more protrusions configured to slidingly couple with the longitudinal slots, enabling the sheath 36*b* and the rod 32 to translate linearly relative to the handle sleeve 70, without relative rotation therebetween.

FIG. 14C further depict a T-handle 72. The T-handle 72 has an internal lumen 74 that rotationally receives the metal rod 32. The endplate 73 is coupled to the proximal end of the metal rod 32 and prevents the metal rod 32 from exiting the lumen of the T-handle 72. In this manner, the T-handle 72 can rotate relative to the rod 32, but cannot translate axially in relation thereto. The endplate 73 can be coupled to the metal rod 32 using a screw-threaded connection or another coupling means.

The proximal portion of the lumen 71 of the handle sleeve 70 includes a female thread (not shown in the drawings) configured to screw-threadedly couple to the male threads 75 of the T-handle 72. FIGS. 14A and 14B illustrate that because the T-handle 72 is screw-threadedly coupled to the handle sleeve 70, rotation of the T-handle 72 relative to the handle sleeve 70 causes the sheath 36*b*, the metal rod 32, and the abrading head 34 translate axially relative to the handle sleeve 70, which remains stationary.

FIG. 14A depicts a configuration of the joint decorticator 30*b* in which the T-handle 72 is fully screwed into the handle sleeve 70. In this closed configuration, the distance between the abrading head 34 and the distal end of the handle sleeve 70 is $L_1$. FIG. 14B depicts a configuration of the joint decorticator 30*b* in which the T-handle 72 is an unscrewed position relative the handle sleeve 70. In this extended configuration, the distance between the abrading head 34 and the distal end of the handle sleeve 70 is $L_2$, which is less than the distance $L_1$.

Figure 15A:
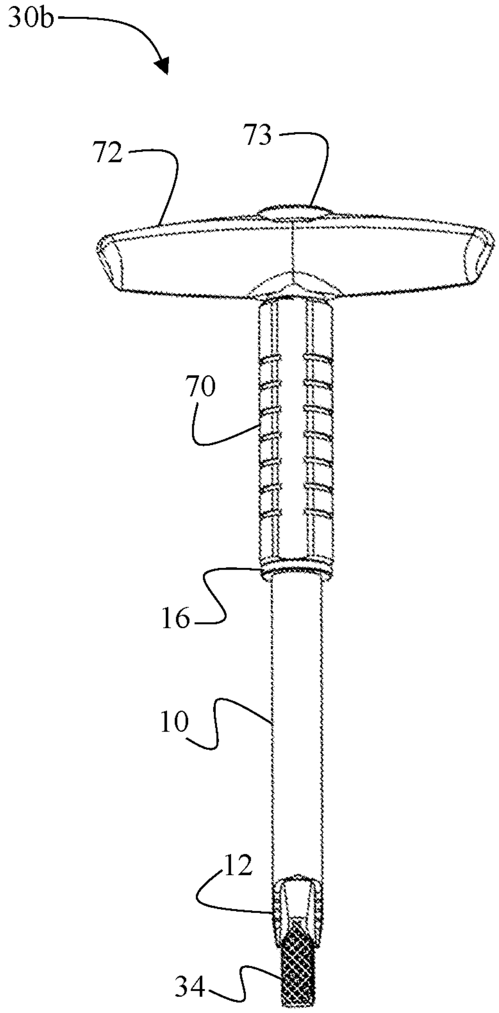
FIG. 15A is the first figure in a sequence illustrating the method of using the threaded-handle extraction mechanism, wherein the shaft of the joint decorticator is inserted into the working channel and the threaded handle in the closed position.
Figure 15B:
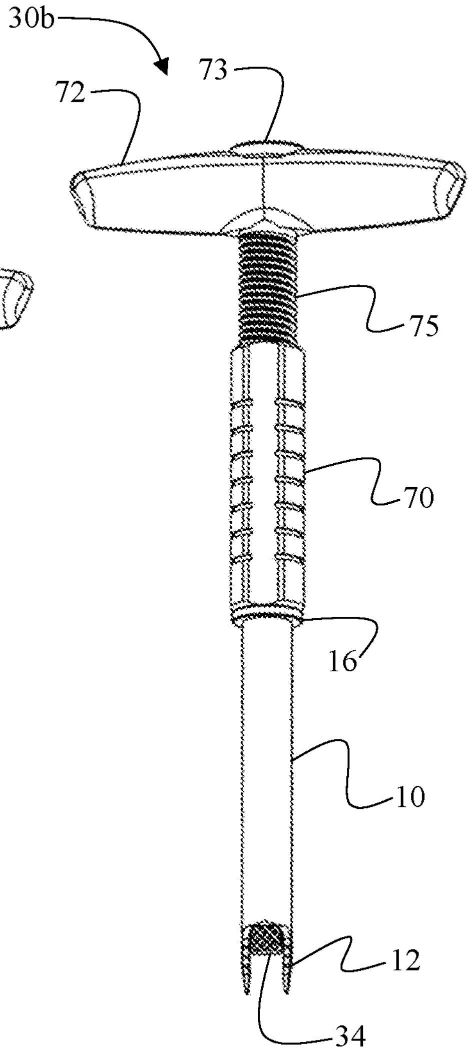
FIG. 15B is the second figure in a sequence illustrating the method of using the threaded-handle extraction mechanism, wherein the threaded handle is in the extended position causing the abrading head to retract into the working channel.

FIG. 15A depicts that in the closed configuration, the distance between the terminal end of the abrading head and the distal end of the handle sleeve 70 exceeds the length the working channel 10. Therefore, when the joint decorticator 30*b* is fully inserted into the working channel 10, the abrading head 34 sufficiently protrudes out of the lumen of the working channel 10 to create an implant-receiving void within the sacroiliac joint. The endplate 73 of the T-handle 72 may be configured to be impacted by a mallet, or another impactor device, to drive the abrading head 34 into the sacroiliac joint.

To extract the abrading head 34 from the sacroiliac joint, a surgeon may apply a manual linear retraction force onto the T-handle 72. In some circumstances, a manual force applied to the T-handle 72 may be insufficient to dislodge the abrading head 34. In such cases, the surgeon would rotate the T-handle 72 while holding the handle sleeve 70 stationary, thereby causing the sheath 36*b* and the rod 32 to axially retract relative to the handle sleeve 70. As the surgeon continues rotating the T-handle 72, the distance between the distal end of the handle sleeve 70 and the terminal end of the abrading head 34 decreases, thereby retracting the abrading head 34 into the lumen of the working channel 10, thereby dislodging the abrading head 34 from the sacroiliac joint.

Integrated Slide-Hammer Extraction Mechanism

Figure 16A:
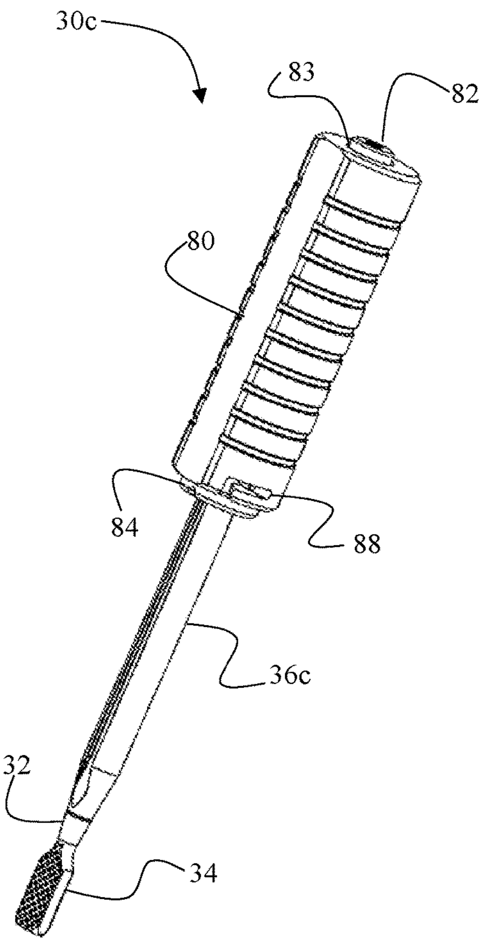
FIG. 16A is a perspective view of an embodiment of a joint decorticator having an integrated slide hammer and a mallet head.
Figure 16B:
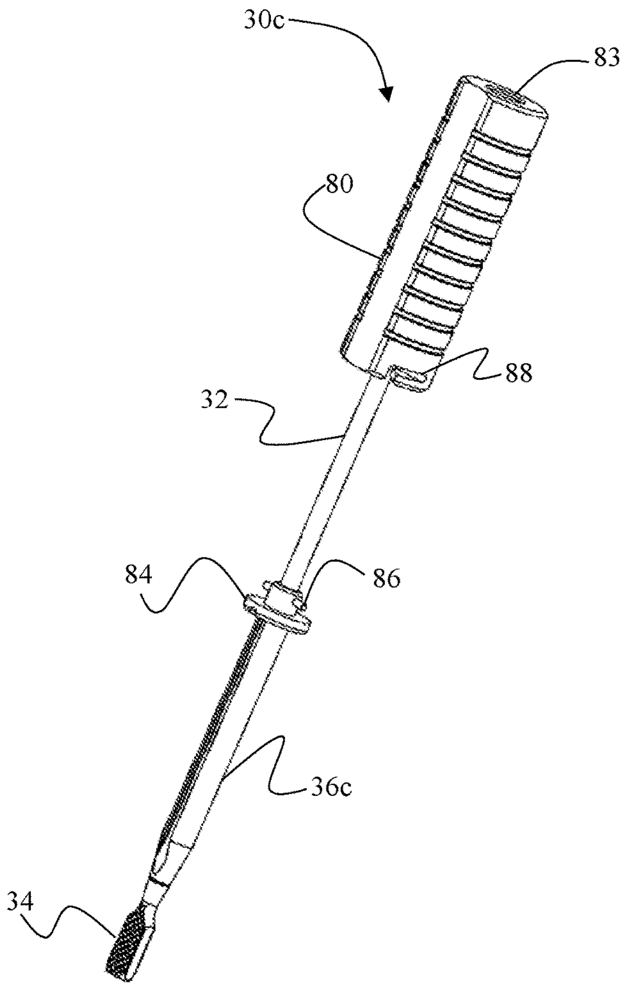
FIG. 16B is a perspective view of an embodiment of a joint decorticator having an integrated slide hammer and a pull-handle and a mallet head.

FIGS. 16A and 16B depict an embodiment of a joint decorticator 30*c* having an integrated slide hammer extraction mechanism. In this embodiment, the metal rod 32 is secured within a polymer sheath 36*c*. A hammer sleeve 80 has an internal lumen 83 that receives the proximal end of the metal rod 32 therein. The hammer sleeve 80 is able to translate axially and angularly relative to the metal rod 32. An endplate 82 is coupled to the proximal end of the metal rod 32. The distal portion of the internal lumen 83 of the hammer sleeve 80 has a neck portion whose diameter is less than the diameter of the endplate 82. In this manner, the retractive axial movement of the hammer sleeve 80 relative to the metal rod 32 encounters a mechanical stop when the neck portion of the hammer sleeve 80 engages the endplate 82.

The sheath 36*c* has a stop collar 84 configured to function as a mechanical stop for the joint decorticator 30 when it is inserted into the working channel 10. One or more locking pins 86 extend from the proximal portion of the sheath 36*c*. The distal end of the hammer sleeve 80 has an L-shaped groove 88. FIG. 16A depicts that the groove 88 is configured to receive the locking pin 86 therein. Upon entry of the locking pin 86 into the groove 88, the hammer sleeve 80 can be rotated to advance the locking pin 86 within the circumferential portion of groove 82, thereby locking the hammer sleeve 80 to the sheath 36*c*, as depicted in FIG. 16A. In this locked configuration, the hammer sleeve 80 functions as a handle of the joint decorticator 30*c*.

To release the hammer sleeve 80 from the sheath 36*c*, the surgeon would rotate the hammer sleeve 80 in the opposite direction until the locking pin 86 is aligned with the opening of the groove 88, at which point, the surgeon can pull the hammer sleeve 80 to transition the slide hammer into its operating configuration, as depicted in FIG. 16B. In this operating configuration, the hammer sleeve 80 can slide along the metal rod 32 until the neck portion of the internal lumen 83 of the hammer sleeve 80 impacts the underside of the implant 82. This impact force is transferred to the metal rod 32, thus extracting the abrading head 34 from the sacroiliac joint.

Multi-Functional Hammer Sleeve/Impactor

Figure 17A:
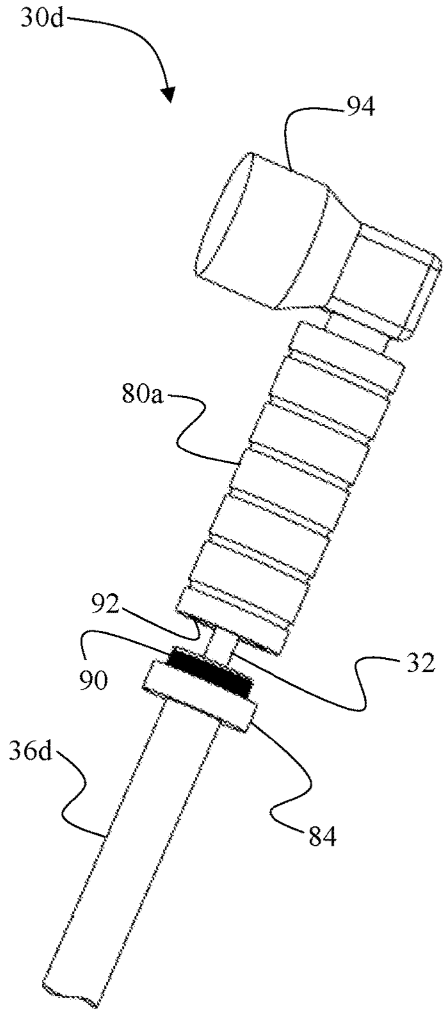
FIG. 17A is a perspective view of an embodiment of a joint decorticator having an integrated slide hammer.

FIG. 17A depicts an embodiment of the joint decorticator 30*d*. Similarly to the embodiment 30*c*, the joint decorticator 30*d* has a hammer sleeve 80*a*. The locking mechanism for hammer sleeve 80*a* comprises a male thread 90 disposed on the proximal end of sheath 36*d* configured to couple to a female thread 92 disposed within the distal portion of the internal lumen of the hammer sleeve 80*a*. When the threads 90 and 92 are coupled, the hammer sleeve 80*a* is in its locked configuration, wherein the hammer sleeve 80*a* functions as a handle of the joint decorticator 30*d*. When the threads 90 and 92 are disengaged, as depicted in FIG. 17A, the hammer sleeve 80*a* is in its operating configuration and can be used as a slide hammer for dislodging and extracting the abrading head 34 from the sacroiliac joint, as disclosed above with respect to the joint decorticator 30*c*.

In addition, FIG. 17A depicts that the hammer sleeve 80*a* has a mallet head 94, which enables the joint decorticator 30*d* to be used as a mallet (while the hammer sleeve 80*a* is in the closed configuration) for impacting other surgical instruments, for example the joint dilator 20. The advantage of such dual-functionality is that when surgical instruments are provided as a kit, a dedicated mallet may be eliminated because the mallet head 94 of the joint decorticator 30*d* performs that function.

Figure 17B:
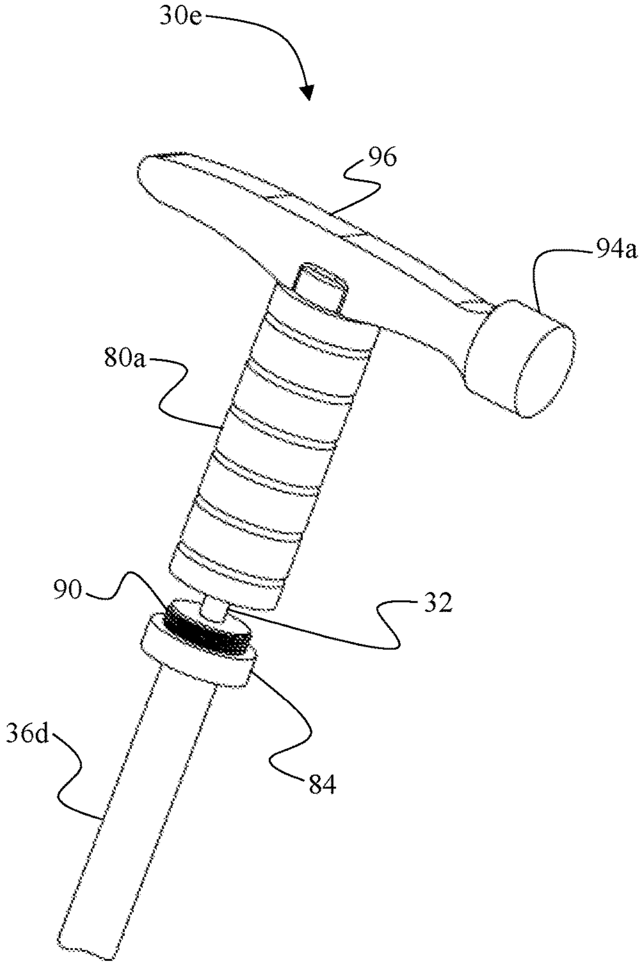
FIG. 17B is a perspective view of the joint having an integrated slide hammer, with the hammer sleeve in an operating configuration.

FIG. 17B depicts an embodiment of the joint decorticator 30*e*. This embodiment is similar to the joint decorticator 30*d*, but the mallet head 94*a* further includes a pull-handle 96. The pull-handle 96 is configured to be grasped by a surgeon enabling the surgeon to exert an axial force onto the pull-handle 96 to manually dislodge the abrading head 34 from the patient's sacroiliac joint and remove the joint decorticator 30*d* from the working channel 10. If such attempt is unsuccessful, the surgeon can utilize the integrated slide hammer by unscrewing the hammer sleeve 80*a* from the sheath 36*d*, thereby transitioning it into the operating configuration.

Cable Loop Extraction Mechanism

Figure 18:
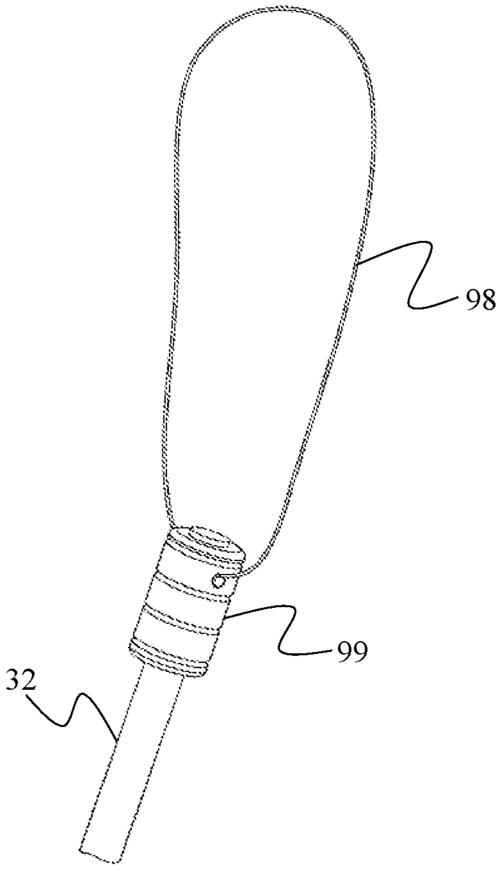
FIG. 18 is a perspective view of an embodiment of an embodiment of a joint decorticator having a cable-loop extraction mechanism.

In an embodiment depicted in FIG. 18, a cable loop 98 may be integrated into the proximal end the handle 99 of the joint decorticator. To dislodge the abrading head 34 from the sacroiliac joint, a surgeon would grasp the cable loop 98 and would apply a pulling force thereto. If the manual pulling force in insufficient to dislodge the abrading head 34, then the surgeon can use an impact tool—such as a mallet—to impact the section of the cable loop 98 opposite the handle 99 from within the cable loop 98. The force of the impact is translated from the cable loop 98 to the handle 99, which is connected to the abrading head 34. In this manner, the impact applied onto the cable loop 98 is translated to the abrading head, dislodging it from the sacroiliac joint.

The foregoing embodiments are merely representative of the sacroiliac fusion instruments and are not meant for limitation of the invention. For example, persons skilled in the art would readily appreciate that there are several embodiments and configurations of the dual-material construction and the extraction mechanisms described herein. As another example, the alignment means described herein comprise channels disposed on the surgical instruments configured to receive an alignment protrusion disposed on the working channel. However, persons skilled in the art will recognize that these alignment means can be reversed, whereby the alignment protrusion can be disposed on the surgical instruments while the longitudinal channel can be disposed within the working channel. In addition, multiple extraction mechanisms disclosed herein are alternatives and are not mutually exclusive—instead, they can be implemented in combinations with one another without departing from the envisioned invention. Consequently, it is understood that equivalents and substitutions for certain elements and components set forth above are part of the invention described herein, and the true scope of the invention is set forth in the claims below.

What is claimed is:

1. A decorticator apparatus for preparing a joint for receipt of a bone fusion implant, comprising:

- a sheath having a lumen therein, a distal end, and a proximal end, the sheath configured to be inserted into a working channel providing access to the joint;
- a rod disposed within the lumen of the sheath in an immobilized relation thereto, the rod having a first end and a second end;
- an abrading head disposed on the first end of the rod and extending beyond the distal end of the sheath, the abrading head having an abrading surface configured to abrade a cortical bone layer within the joint; and
- an extraction lever pivotally affixed to the sheath, the extraction lever having a cam mechanism configured to apply a retraction force onto the working channel as the extraction lever is pivotally transitioned from a closed position toward an open position, thereby retracting the abrading head of the decorticator apparatus into the working channel.

2. The decorticator apparatus of claim 1, wherein the cam mechanism comprises two cam members disposed on opposite sides of the sheath defining a gap therebetween configured to accommodate the sheath as the extraction lever is pivoted from the closed position toward the open position.

3. The decorticator apparatus of claim 1, wherein the sheath comprises a first handle portion and the extraction lever comprises a second handle portion, wherein the first and the second handle portions collectively define a handle of the decorticator apparatus when the extraction lever is in the closed position.

4. The decorticator apparatus of claim 3, further comprising a fillet at an interface of the cam mechanism and the second handle portion.

5. The decorticator apparatus of claim 1, wherein in the closed position the cam mechanism is disposed on an opposite side of the rod relative to a pivot axis of the extraction lever.

6. The decorticator apparatus of claim 1, wherein an opening of a longitudinal channel of the sheath has a delta shape configured to guide an alignment protrusion of the working channel into the longitudinal channel of the sheath.

7. The decorticator apparatus of claim 1, wherein the decorticator apparatus is configured to receive an extraction tool, wherein the extraction tool is configured to simultaneously apply opposing forces onto the decorticator apparatus and the working channel, thereby causing the abrading head of the decorticator apparatus to retract into the working channel.

8. The decorticator apparatus of claim 7, wherein the decorticator apparatus has two engagement surfaces for engagement with the extraction tool, a second engagement surface being disposed at a more distal position along the decorticator apparatus relative to a first engagement surface, wherein the extraction tool is configured to sequentially operably engage the first and the second engagement surfaces, whereby each operable engagement results in an incremental extraction of the decorticator apparatus from the working channel.

9. The decorticator apparatus of claim 1, wherein the sheath is configured to connect to an extraction tool, whereby the extraction tool forms a lateral surface relative to the decorticator apparatus, wherein an extraction force is applied onto the extraction tool to extract the decorticator apparatus from the working channel.

10. The decorticator apparatus of claim 9, wherein the extraction tool has an underside surface oriented toward to the distal end of the sheath, and wherein the extraction force is applied by striking the underside surface of the extraction tool with an impactor.

11. The decorticator apparatus of claim 1, further comprising an impact disk disposed on the second end of the rod and extending beyond the proximal end of the sheath, the impact disk configured for being struck with an impactor, whereby the rod is configured to transfer an impact force from the impact disk to the abrading head thereby driving the abrading head into the joint.

12. A method of preparing a joint for receipt of a bone fusion implant, comprising:

- inserting a working channel into the joint;
- inserting an abrading head of a decorticator apparatus into the working channel, the decorticator apparatus comprising:
  - a sheath having a lumen therein, a distal end, and a proximal end, the sheath configured for insertion into the working channel providing access to the joint;
  - a rod disposed within the lumen of the sheath in an immobilized relation thereto, the rod having a first end and a second end; and
  - the abrading head disposed on the first end of the rod and extending beyond the distal end of the sheath, the abrading head having an abrading surface configured to abrade a cortical bone layer within the joint;
- advancing the decorticator apparatus into the working channel;
- driving the abrading head of the decorticator apparatus into the joint, thereby causing the abrading head to abrade the cortical bone layer within the joint; and
- pivotally transitioning an extraction lever from a closed position toward an open position, wherein the extraction lever is pivotally affixed to the sheath and has a cam mechanism configured to apply a force onto the working channel as the extraction lever is transitioned from the closed position toward the open position, thereby retracting the abrading head of the decorticator apparatus into the working channel.

13. The method of claim 12, wherein as the extraction lever is transitioned from the closed position toward the open position the sheath enters into a gap defined between two cam members disposed on opposite sides of the sheath and collectively defining the cam mechanism.

14. The method of claim 12, further comprising articulating a handle assembly of the decorticator apparatus, wherein the handle assembly comprises a first handle portion disposed on the sheath and a second handle portion disposed on the extraction lever.

15. The method of claim 13, wherein transitioning the extraction lever from the closed position toward the open position causes the extraction lever to pivot about a pivot axis disposed on the opposite side of the rod relative to the cam mechanism.

16. The method of claim 12, further comprising positioning a delta-shaped opening of a longitudinal channel of the sheath proximal to an alignment protrusion of the working channel, wherein the delta-shaped opening is configured to guide the alignment protrusion of the working channel into the longitudinal channel of the sheath as the decorticator apparatus is advanced into the working channel.

17. The method of claim 12, further comprising inserting an extraction tool between the working channel and a first engagement surface of the decorticator apparatus and pressing onto a free end of the extraction tool, wherein the extraction tool is configured to simultaneously apply opposing forces onto the decorticator apparatus and the working channel, thereby causing the abrading head of the decorticator apparatus to retract into the working channel.

18. The method of claim 17, further comprising the step of inserting the extraction tool between a second engagement surface of the decorticator apparatus and the working channel, and pressing onto the free end of the extraction tool, wherein the second engagement surface is disposed in a more distal position along the decorticator apparatus in relation to the first engagement surface.

* * * * *